United States Patent
Smith et al.

(10) Patent No.: US 11,076,820 B2
(45) Date of Patent: Aug. 3, 2021

(54) TOMOSYNTHESIS WITH SHIFTING FOCAL SPOT X-RAY SYSTEM USING AN ADDRESSABLE ARRAY

(71) Applicant: HOLOGIC, INC., Marlborough, MA (US)

(72) Inventors: Andrew P. Smith, Marlborough, MA (US); John Laviola, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 45 days.

(21) Appl. No.: 16/095,416

(22) PCT Filed: Apr. 21, 2017

(86) PCT No.: PCT/US2017/028934
§ 371 (c)(1),
(2) Date: Oct. 22, 2018

(87) PCT Pub. No.: WO2017/185028
PCT Pub. Date: Oct. 26, 2017

(65) Prior Publication Data
US 2020/0352531 A1    Nov. 12, 2020

Related U.S. Application Data

(60) Provisional application No. 62/326,451, filed on Apr. 22, 2016.

(51) Int. Cl.
*A61B 6/00*    (2006.01)
*A61B 6/02*    (2006.01)
(Continued)

(52) U.S. Cl.
CPC .............. *A61B 6/405* (2013.01); *A61B 6/025* (2013.01); *A61B 6/4021* (2013.01);
(Continued)

(58) Field of Classification Search
None
See application file for complete search history.

(56) References Cited

U.S. PATENT DOCUMENTS 3,365,575 A    1/1968    Strax
3,502,878 A    3/1970    Stewart
(Continued)

FOREIGN PATENT DOCUMENTS

CN    102222594    10/2011
DE    19820243    11/1999
(Continued)

OTHER PUBLICATIONS

"Essentials for life: Senographe Essential Full-Field Digital Mammography system", GE Health-care Brochure, MM-0132-05.06-EN-US, 2006, 12 pgs.
(Continued)

*Primary Examiner* — Edwin C Gunberg
(74) *Attorney, Agent, or Firm* — Merchant & Gould P.C.

(57) ABSTRACT

A tomosynthesis system has an x-ray source with an addressable array of electron emitting sections on the cathode. The x-ray source moves rotationally about an imaging target, such as a breast. During the rotation, x-rays are emitting from the x-ray source while the x-ray source continues to move. During the emission of x-rays, different subsets of electron-emitting sections of the addressable array are activated to compensate for movement of the x-ray source. By activating the different subsets of electron-emitting sections, an effective focal spot of the x-ray position appears to retain the same shape, size, and position from the perspective of the imaging target, despite movement of the x-ray source itself.

25 Claims, 18 Drawing Sheets

Tomosynthesis System 100

(51) Int. Cl.
  *H01J 35/06* (2006.01)
  *H01J 35/10* (2006.01)
(52) U.S. Cl.
  CPC ............ *A61B 6/4476* (2013.01); *A61B 6/502* (2013.01); *H01J 35/065* (2013.01); *H01J 35/10* (2013.01); *H01J 2201/30469* (2013.01); *H01J 2235/068* (2013.01)

(56) References Cited

U.S. PATENT DOCUMENTS

| | | |
|---|---|---|
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 4,998,270 A | 3/1991 | Scheid et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,142,557 A | 8/1992 | Toker |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,240,011 A | 8/1993 | Assa |
| 5,256,370 A | 10/1993 | Slattery et al. |
| 5,274,690 A | 12/1993 | Burke et al. |
| 5,289,520 A | 2/1994 | Pellegrino et al. |
| 5,291,539 A | 3/1994 | Thumann et al. |
| 5,313,510 A | 5/1994 | Ebersberger et al. |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,469,429 A | 11/1995 | Yamazaki et al. |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,812,632 A | 9/1998 | Schardt et al. |
| 5,818,898 A | 10/1998 | Tsukamoto et al. |
| 5,828,722 A | 10/1998 | Ploetz et al. |
| 5,841,829 A | 11/1998 | Dolazza et al. |
| 5,844,965 A | 12/1998 | Galkin |
| 5,864,146 A | 1/1999 | Karellas |
| 5,872,828 A | 2/1999 | Niklason et al. |
| 5,878,104 A | 3/1999 | Ploetz |
| 5,896,437 A | 4/1999 | Ploetz |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,167,115 A | 12/2000 | Inoue |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,252,935 B1 | 6/2001 | Styrnol et al. |
| 6,256,369 B1 | 7/2001 | Lai |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,459,925 B1 | 10/2002 | Nields et al. |
| 6,480,565 B1 | 11/2002 | Ning |
| 6,490,476 B1 | 12/2002 | Townsend et al. |
| 6,501,819 B2 | 12/2002 | Unger et al. |
| 6,542,575 B1 | 4/2003 | Schubert et al. |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,895,076 B2 | 5/2005 | Halsmer et al. |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,940,943 B2 | 9/2005 | Claus et al. |
| 6,950,492 B2 | 9/2005 | Besson |
| 6,950,493 B2 | 9/2005 | Besson |
| 6,957,099 B1 | 10/2005 | Arnone et al. |
| 6,970,531 B2 | 11/2005 | Eberhard et al. |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer et al. |

(56) References Cited

U.S. PATENT DOCUMENTS

| | | |
|---|---|---|
| 7,016,461 B2 | 3/2006 | Rotondo et al. |
| 7,110,490 B2 | 9/2006 | Eberhard et al. |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,578 B2 | 3/2007 | Bang et al. |
| 7,190,758 B2 | 3/2007 | Hagiwara |
| 7,206,462 B1 | 4/2007 | Betke |
| 7,244,063 B2 | 7/2007 | Eberhard et al. |
| 7,245,694 B2 | 7/2007 | Jing et al. |
| 7,286,645 B2 | 10/2007 | Freudenberger et al. |
| 7,302,031 B2 | 11/2007 | Hjarn et al. |
| 7,315,607 B2 | 1/2008 | Ramsauer |
| 7,319,734 B2 | 1/2008 | Besson |
| 7,319,735 B2 | 1/2008 | Defreitas et al. |
| 7,319,736 B2 | 1/2008 | Rotondo et al. |
| 7,323,692 B2 | 1/2008 | Rowlands et al. |
| 7,331,264 B2 | 2/2008 | Ozawa |
| 7,356,113 B2 | 4/2008 | Wu et al. |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,616,731 B2 | 11/2009 | Pack et al. |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | Defreitas et al. |
| 7,839,979 B2 | 11/2010 | Hauttmann et al. |
| 7,869,563 B2 | 1/2011 | Defreitas et al. |
| 7,881,428 B2 | 2/2011 | Jing et al. |
| 7,885,384 B2 | 2/2011 | Mannar et al. |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig et al. |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 | 10/2014 | O'Connor |
| 8,873,716 B2 | 10/2014 | Ren et al. |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,460,508 B2 | 10/2016 | Gkanatsios et al. |
| 9,498,175 B2 | 11/2016 | Stein et al. |
| 9,502,148 B2 | 11/2016 | Ren et al. |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,452,252 B2 | 10/2019 | Gkanatsios et al. |
| 10,638,994 B2 | 5/2020 | DeFreitas |
| 10,719,223 B2 | 7/2020 | Gkanatsios |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 | 7/2002 | Dolazza |
| 2002/0122533 A1 | 9/2002 | Marie et al. |
| 2002/0126798 A1 | 9/2002 | Harris et al. |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |
| 2003/0058989 A1 | 3/2003 | Rotondo et al. |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer et al. |
| 2004/0213378 A1* | 10/2004 | Zhou ............... A61B 6/508 378/122 |
| 2004/0247081 A1 | 12/2004 | Halsmer et al. |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard et al. |
| 2005/0135555 A1 | 6/2005 | Claus et al. |
| 2005/0135664 A1 | 6/2005 | Kaufhold et al. |
| 2005/0147205 A1 | 7/2005 | Dolazza et al. |
| 2005/0226375 A1 | 10/2005 | Eberhard et al. |
| 2005/0248347 A1 | 11/2005 | Damadian |
| 2006/0030784 A1 | 2/2006 | Miller et al. |
| 2006/0034426 A1 | 2/2006 | Freudenberger et al. |
| 2006/0074288 A1 | 4/2006 | Kelly |
| 2006/0098855 A1 | 5/2006 | Gkanatsios et al. |
| 2006/0109951 A1 | 5/2006 | Popescu |
| 2006/0126780 A1 | 6/2006 | Rotondo et al. |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |

(56) References Cited

U.S. PATENT DOCUMENTS

| | | |
|---|---|---|
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack et al. |
| 2008/0101537 A1 | 5/2008 | Sendai |
| 2008/0112534 A1 | 5/2008 | Defreitas |
| 2008/0118023 A1 | 5/2008 | Besson |
| 2008/0130979 A1 | 6/2008 | Ren |
| 2008/0212861 A1 | 9/2008 | Durgan et al. |
| 2008/0247504 A1 | 10/2008 | Edic et al. |
| 2008/0285712 A1 | 11/2008 | Kopans et al. |
| 2008/0317196 A1 | 12/2008 | Imai |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0141859 A1 | 6/2009 | Gkanatsios et al. |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0296882 A1 | 12/2009 | Gkanatsios |
| 2009/0304147 A1 | 12/2009 | Jing et al. |
| 2010/0020937 A1 | 1/2010 | Hautmann et al. |
| 2010/0020938 A1 | 1/2010 | Koch et al. |
| 2010/0034450 A1 | 2/2010 | Mertelmeier |
| 2010/0054400 A1 | 3/2010 | Ren |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar et al. |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren et al. |
| 2010/0313196 A1 | 12/2010 | De Atley et al. |
| 2011/0026667 A1 | 2/2011 | Poorter |
| 2011/0069809 A1 | 3/2011 | Defreitas et al. |
| 2011/0178389 A1 | 7/2011 | Kumar et al. |
| 2011/0188624 A1 | 8/2011 | Ren et al. |
| 2011/0234630 A1 | 9/2011 | Batman et al. |
| 2011/0268246 A1 | 11/2011 | Dafni |
| 2012/0033868 A1 | 2/2012 | Ren et al. |
| 2012/0051502 A1 | 3/2012 | Ohta et al. |
| 2012/0236987 A1 | 9/2012 | Ruimi |
| 2012/0238870 A1 | 9/2012 | Smith et al. |
| 2013/0028374 A1 | 1/2013 | Gkanatsios et al. |
| 2013/0211261 A1 | 8/2013 | Wang |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2016/0106383 A1 | 4/2016 | Ren et al. |
| 2016/0189376 A1 | 6/2016 | Bernard |
| 2016/0209995 A1 | 7/2016 | Jeon |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0302746 A1 | 10/2016 | Erhard |
| 2016/0331339 A1 | 11/2016 | Guo |
| 2017/0024113 A1 | 1/2017 | Gkanatsios et al. |
| 2017/0032546 A1 | 2/2017 | Westerhoff |
| 2017/0071562 A1 | 3/2017 | Suzuki |
| 2017/0128028 A1 | 5/2017 | DeFreitas et al. |
| 2017/0135650 A1 | 5/2017 | Stein et al. |
| 2017/0316588 A1 | 11/2017 | Homann |
| 2017/0319167 A1 | 11/2017 | Goto |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0344276 A1 | 12/2018 | DeFreitas et al. |
| 2019/0059830 A1 | 2/2019 | Williams |
| 2019/0095087 A1 | 3/2019 | Gkanatsios et al. |
| 2019/0200942 A1 | 7/2019 | DeFreitas |
| 2019/0336794 A1 | 11/2019 | Li |
| 2019/0388051 A1 | 12/2019 | Morita |
| 2020/0012417 A1 | 1/2020 | Gkanatsios |
| 2020/0029927 A1 | 1/2020 | Wilson |
| 2020/0085393 A1 | 3/2020 | Zhang |

FOREIGN PATENT DOCUMENTS

| | | |
|---|---|---|
| DE | 102004017540 | 10/2005 |
| DE | 102004051401 | 5/2006 |
| DE | 102004051820 | 5/2006 |
| DE | 10 2010 027 871 A1 | 10/2011 |
| EP | 0775467 | 5/1997 |
| EP | 0982001 | 3/2000 |
| EP | 1028451 | 8/2000 |
| EP | 1428473 | 6/2004 |
| EP | 1623672 | 2/2006 |
| EP | 1759637 | 3/2007 |
| EP | 1569556 | 4/2012 |
| EP | 2732764 | 5/2014 |
| EP | 2602743 | 11/2014 |
| EP | 2 819 145 A1 | 12/2014 |
| EP | 3143935 | 3/2017 |
| JP | 53151381 U | 11/1978 |
| JP | H05329143 | 12/1993 |
| JP | 2000287960 | 10/2000 |
| JP | 2001-346786 | 12/2001 |
| JP | 2002219124 | 8/2002 |
| JP | 2004511884 | 4/2004 |
| JP | 2004188200 | 7/2004 |
| JP | 2005142160 | 6/2005 |
| JP | 2006519625 | 8/2006 |
| JP | 2006-231054 | 9/2006 |
| JP | 2007-50264 | 3/2007 |
| JP | 2007054528 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2008159317 | 7/2008 |
| JP | 2009500048 | 1/2009 |
| JP | 2011516116 | 5/2011 |
| JP | 2012-509714 | 4/2012 |
| JP | 2012-511988 | 5/2012 |
| JP | 2015-530706 | 10/2015 |
| WO | WO 90/05485 | 5/1990 |
| WO | WO 9803115 | 1/1998 |
| WO | WO 98/16903 | 4/1998 |
| WO | WO 00/51484 | 9/2000 |
| WO | WO 03/020114 | 3/2003 |
| WO | WO 03037046 | 5/2003 |
| WO | WO 2003/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006055830 | 5/2006 |
| WO | WO 2006/058160 | 6/2006 |
| WO | WO 2006058160 | 6/2006 |
| WO | WO 2007129244 | 11/2007 |
| WO | WO 2008072144 | 6/2008 |
| WO | WO 2009012453 | 1/2009 |
| WO | WO 2009122328 | 10/2009 |

(56) References Cited

FOREIGN PATENT DOCUMENTS

| WO | WO 2009136349 | 11/2009 |
|---|---|---|
| WO | WO 2010060007 | 5/2010 |
| WO | 2010/070554 A1 | 6/2010 |
| WO | 2013/184213 A2 | 12/2013 |

OTHER PUBLICATIONS

"Filtered Back Projection," (NYGREN) published May 8, 2007; URL:http://web.archive.org/web/19991010131715/http://owlnet.rice.edu/-.about.elec539/Projects97/cult/node2.html., 2 pgs.

"Lorad Selenia" Document B-BI-SEO US/Intl (May 2006) copyright Hologic 2006, 12 pgs.

Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.

American College of Radiology website, located at http://www.acr.org/FAQs/DBT-FAQ, "Digital Breast Tomosynthesis FAQ for Insurers", obtained online on Dec. 8, 2015, 2 pages.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.

Chan, Heang-Ping et al., "ROC study of the effect of stereoscopic imaging on assessment of breast lesions", Medical Physics, vol. 32, No. 4, Apr. 2005, 7 pgs.

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98-5493, Nov. 1998, 8 pgs.

Dobbins, James T., "Digital x-ray tomosynthesis: current state of the art and clinical potential," Physics in Medicine and Biology, Taylor and Francis Ltd, London GB, vol. 48, No. 19, Oct. 7, 2003, 42 pages.

Grant, David G., "Tomosynthesis: a three-dimensional imaging technique", IEEE Trans. Biomed. Engineering, vol. BME-19, #1, Jan. 1972, pp. 20-28.

Japanese Office Action mailed in Application 2016-087710, dated Mar. 1, 2017, 5 pages.

Japanese Office Action dated in Application 2017-001579, dated Mar. 29, 2017, 1 page. (No English Translation.).

Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Mammographic Accreditation Phantom, http://www.cirsinc.com/pdfs/015cp.pdf. (2006), 2 pgs.

Niklason, Loren T. et al., "Digital Tomosynthesis in Breast Imaging", Radiology, Nov. 1997, vol. 205, No. 2, pp. 399-406.

Pediconi, Federica et al., "Color-coded automated signal intensity-curve for detection and characterization of breast lesions: Preliminary evaluation of a new software for MR-based breast imaging", International Congress Series 1281 (2005) 1081-1086.

Pisano, Etta D., "Digital Mammography", Radiology, vol. 234, No. 2, Feb. 2005, pp. 353-362.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Smith, Andrew, PhD, "Full Field Breast Tomosynthesis", Hologic White Paper, Oct. 2004, 6 pgs.

Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.

Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.

International Search Report and Written Opinion of the International Searching Authority for International Patent Application No. PCT/US2017/028934 dated Sep. 27, 2017, 25 pages.

Bo Zhao et al.: "Imaging performance of an amorphous selenium digital mammography detector in a breast tomosynthesis system", Med. Phys., vol. 35, No. 5, Apr. 24, 2008 (Apr. 24, 2008), XP012116060, DOI: 10.1118/1.2903425.

Guang Yang et al.: "Stationary digital breast tomosynthesis system with a multi-beam field emission x-ray source array", Medical Imaging 2008: Physics of Medical Imaging, Proc. of SPIE, vol. 6913, Mar. 6, 2008 (Mar. 6, 2008), pp. 69131A, XP055652017.

Kachelriess, "Flying Focal Spot (FFS) in Cone-Beam CT", 2004 IEEE Nuclear Science Symposium Conference Record, Oct. 16-22, 2004, Rome Italy, vol. 6, pp. 3759-3763.

PCT International Search Report and Written Opinion from related PCT Application No. PCT/US2009/065451 dated Feb. 5, 2010, 10 pages.

Peter Schardt et al.: "New x-ray tube performance in computed tomography by introducing the rotating envelope tube technology", Med. Phys., vol. 31, No. 8, Aug. 27, 2004 (Aug. 27, 2004), XP012075041.

Yue-Houng Hu et al.: "Image artifacts in digital breast tomosynthesis: Investigation of the effects of system geometry and reconstruction parameters using a linear system approach", Med. Phys., vol. 35, No. 12, Nov. 6, 2008 (Nov. 6, 2008), XP012115818, DOI: 10.1118/1.2996110.

Niklason et al., "Digital breast tomosynthesis: potentially a new method for breast cancer screening", In Digital Mammography, 1998, 6 pages.

Thurfjell, "Mammography screening: one versus two views and independent double reading", Acta Radiologica 35, No. 4, 1994, pp. 345-350.

Japanese Notice of Rejection in Application 2018-554775, dated Feb. 22, 2021, 10 pages.

\* cited by examiner

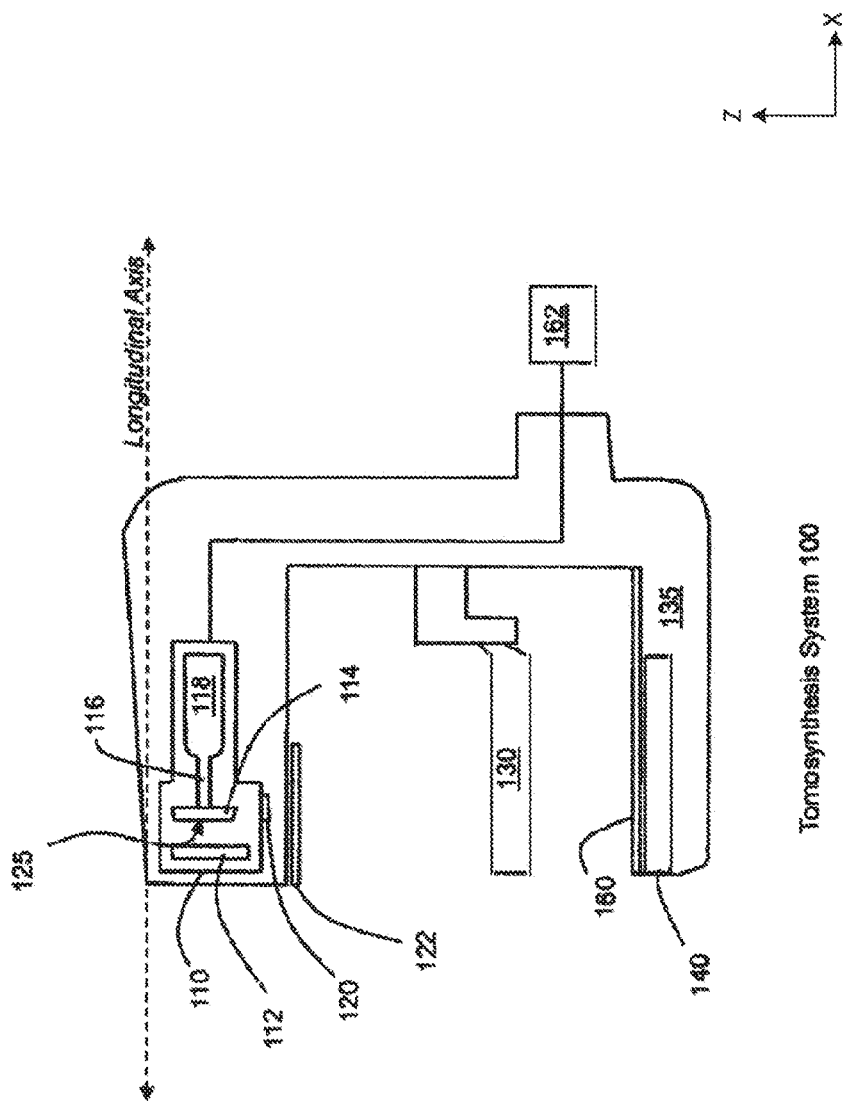

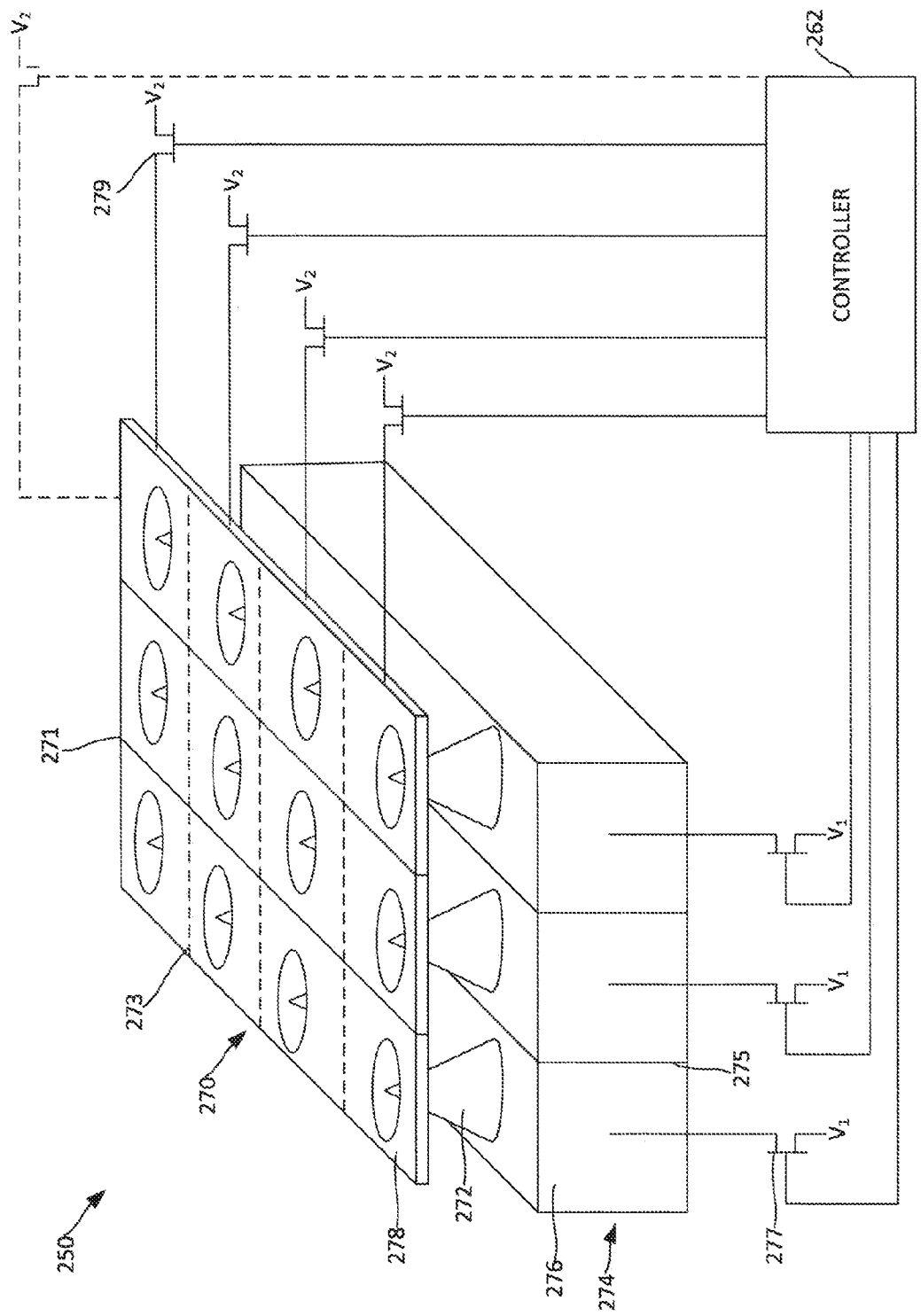

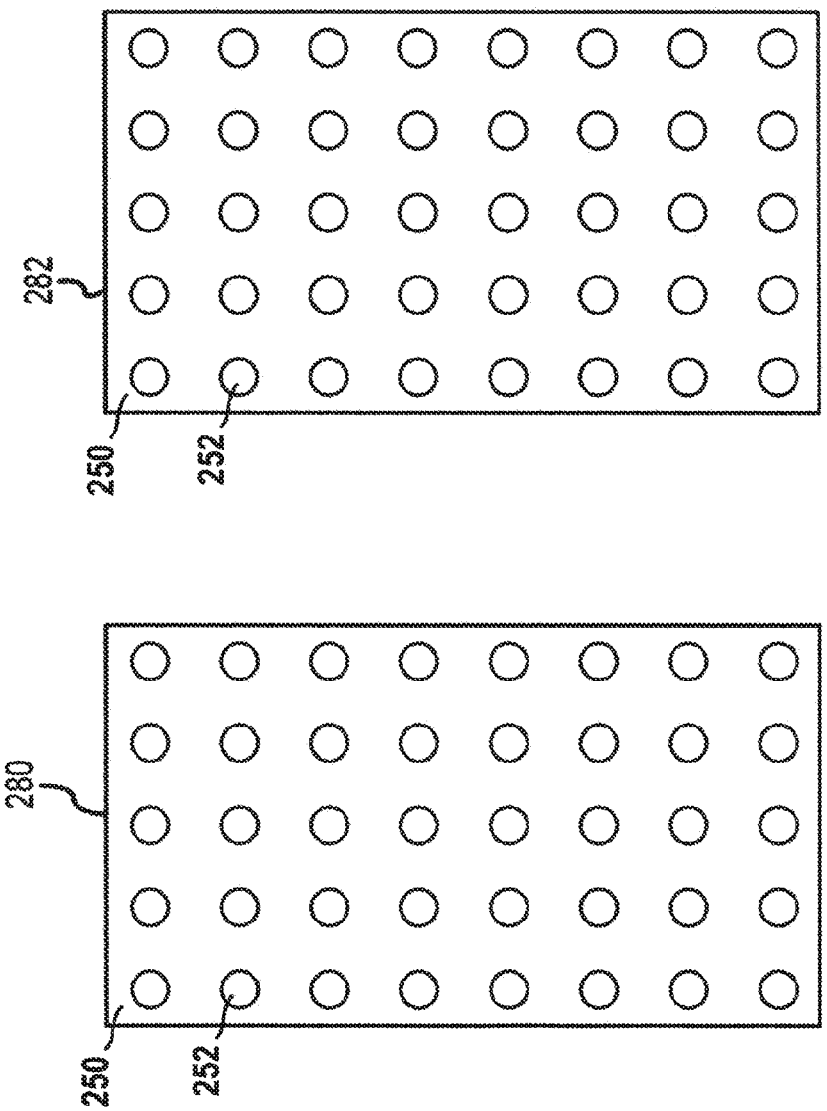

TOMOSYNTHESIS WITH SHIFTING FOCAL SPOT X-RAY SYSTEM USING AN ADDRESSABLE ARRAY

CROSS-REFERENCE TO RELATED APPLICATIONS

This application is a National Stage Application of PCT/US2017/028934, filed Apr. 21, 2017, which claims priority to and the benefit of U.S. Provisional Patent Application Ser. No. 62/326,451, filed Apr. 22, 2016, which is incorporated herein by reference in their entireties. To the extent appropriate, a claim of priority is made to each of the above disclosed applications.

BACKGROUND

Breast tomosynthesis is an imaging technology in which images of a stationary compressed breast are acquired at multiple angles during a short scan. The images are organized as a series of thin high-resolution image "slices" that can be displayed individually or in a dynamic cine mode. Breast tomosynthesis systems move the x-ray source to a variety of different imaging positions relative to an x-ray detector during image acquisition. Reconstructed tomosynthesis slices advantageously reduce or eliminate problems caused by tissue overlap and structure noise in two-dimensional mammography imaging. However, movement of the x-ray source introduces some technological complications.

Typical tomosynthesis systems are arranged to either smoothly and continuously traverse a path during an image scan or utilize stop-and-start scanning procedures. The x-ray source is activated for an exposure time of about 10 ms to 100 ms as the x-ray source moves into each of several imaging locations in the imaging path, and exposure is repeated with a cycle period of 200 ms to 2 seconds. After each exposure the x-ray source is deactivated. As the x-ray source moves between imaging locations the contents of the digital image detector are read out and stored. There is a minimum time period associated with reading the image from the digital detector, and the overall speed of the tomosynthesis scan is determined by the minimum time period for detector read, the exposure time at each location, and the number of exposures. For continuous scans, the x-ray source is moved through space during each exposure period in a tomosynthesis system, which may result in blurring that may reduce diagnostic accuracy.

SUMMARY

In one aspect, the technology relates to a system for radiographic imaging, the system having: a rotating arm configured to rotate relative to a target tissue; a radiation source attached to the rotating arm, the radiation source having a cathode and an anode, wherein the cathode includes an array of electron-emitting sections; and a controller operatively connected to the cathode, the controller configured to activate a first subset of the array of electron-emitting sections when the radiation source is located in a first position relative to the target, and activate a second subset of the array of electron-emitting sections when the radiation source is located in a second position relative to the target. In an embodiment, the rotating arm moves in a first direction and the second subset of the array of electron-emitting sections has electron-emitting sections spaced apart from the first subset of the array of electron-emitting sections in a direction opposite the first direction. In another embodiment, each electron-emitting section includes at least one field emission emitter. In yet another embodiment, each electron-emitting section includes at least one carbon-nanotube emitter. In still another embodiment, the first subset of electron-emitting sections and the second subset of electron-emitting sections are individually addressable by the controller.

In another embodiment of the above aspect, the array has multiple rows of electron-emitting sections, wherein each row is individually addressable by the controller. In an embodiment, each row includes a gate portion and an emitter portion, the gate portion connected to a transistor connected to the controller. In another embodiment, each electron-emitting section is individually addressable by the controller. In yet another embodiment, each electron-emitting section includes a gate portion and an emitter portion, the gate portion connected to a transistor connected to the controller. In still another embodiment, second subset of electron-emitting sections are selected to compensate for movement from the first position to the second position.

In another embodiment of the above aspect, the radiation source is configured to emit radiation to a single location on the target as the radiation source moves from the first position and the second position. In an embodiment, the controller and the radiation source are configured to shift from the first subset of electron-emitting sections to the second subset of electron-emitting sections to maintain the single location as the radiation source moves from the first position and the second position.

In another aspect, the technology relates to a method for radiographic imaging, the method including: moving a radiation source relative to a target from a first position to a second position while emitting radiation from the radiation source to a location of the target, the radiation source including an array of electron-emitting sections; while moving the radiation source from the first position to the second position, activating a first subset of the electron-emitting sections at the first position and activating a second subset of electron-emitting sections at the second position; and detecting the emitted radiation. In an embodiment, the second subset of the array of electron-emitting sections includes electron-emitting sections from the first subset of the array of electron-emitting sections. In another embodiment, each electron-emitting section includes at least one field emission emitter. In yet another embodiment, each electron-emitting section includes at least one carbon-nanotube emitter. In still another embodiment, the array has multiple rows of electron-emitting sections, wherein each row is individually addressable. In another embodiment of the above aspect, each electron-emitting section is individually addressable. In an embodiment, the method includes selecting the second subset of electron-emitting sections to compensate for movement from the first position to the second position.

In another aspect, the technology relates to a method for radiographic imaging, the method including: activating a first subset of electron-emitting sections of a cathode of a radiation source; directing radiation emitted from the radiation source to a location on a target; moving the radiation source relative to the target; and while moving the radiation source, deactivating the first subset of the electron-emitting sections and activating a second subset of electron-emitting sections to maintain the location on the target. In an embodiment, the second subset of electron-emitting sections includes electron-emitting sections from the first subset of electron-emitting sections. In another embodiment, the cathode has multiple rows of electron-emitting sections, and each row is individually addressable. In yet another embodiment, each electron-emitting section includes a single emitter that is individually addressable.

In another aspect, the technology relates to a radiation source, for use in radiographic imaging, comprising a cathode including a three-dimensional addressable array having a plurality of addressable electron-emitting sections. In an embodiment, the three-dimensional addressable array comprises a plurality of a cathode plates. In another embodiment, the three-dimensional addressable array is a v-shaped three-dimensional array. In yet another embodiment, the three-dimensional addressable array is a pyramidal three-dimensional array.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

FIG. 1A depicts a breast tomosynthesis system.

FIG. 2G depicts a portion of an addressable array of field-emission electron emitters on a cathode.

FIG. 2H depicts two cathode plates having addressable arrays of electron-emitting sections.

DETAILED DESCRIPTION

Figure 1B:
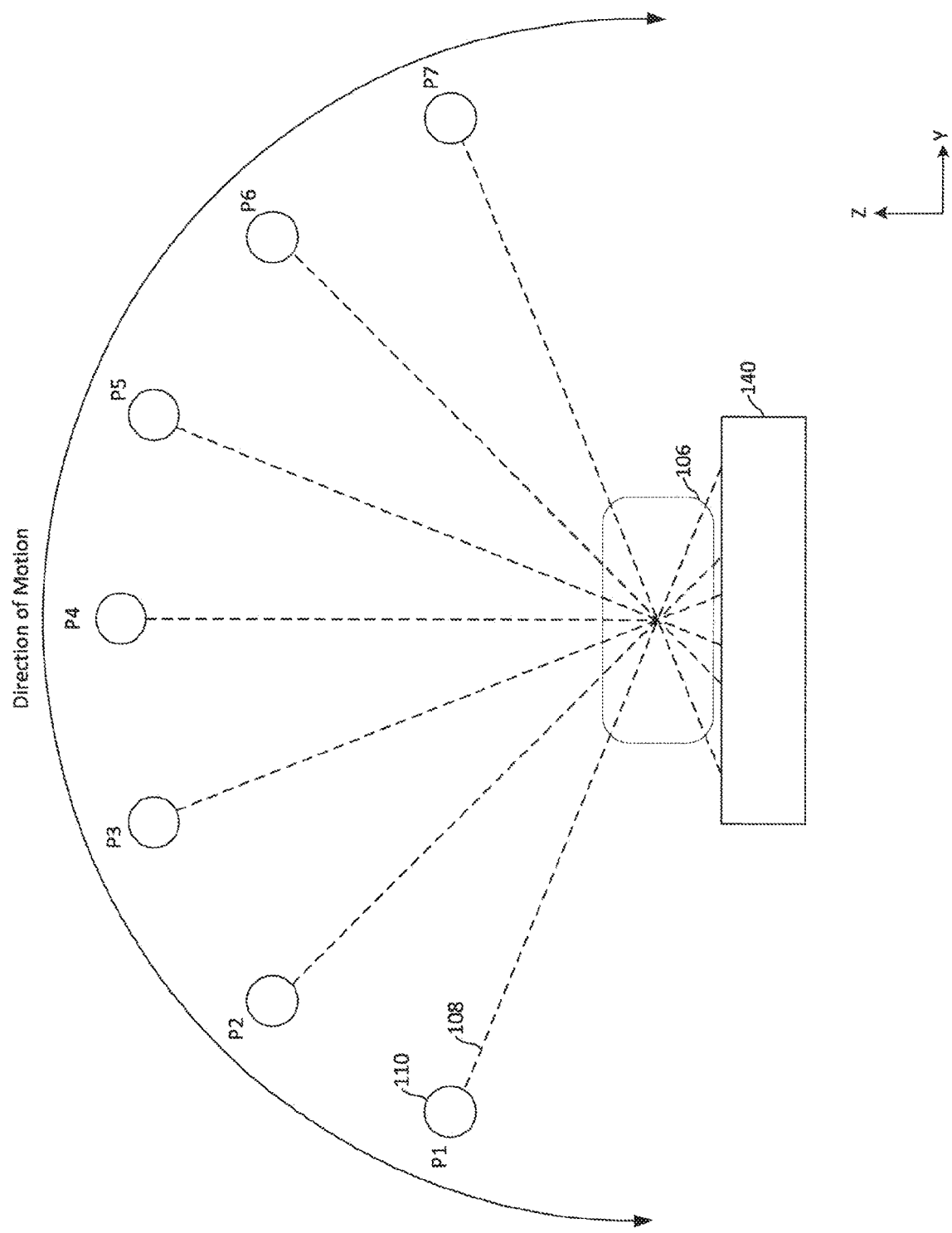
FIG. 1B depicts movement of an x-ray source in a breast tomosynthesis system.

The present technology relates to methods and systems suitable for imaging a target. One particular application for the present technology is for use in breast tomosynthesis. As discussed above, as an x-ray source moves relative to a target, such as a breast, x-rays are emitted from the x-ray source at various positions. In certain examples, the x-ray source does not stop moving during the x-ray emission. The continuous movement causes blurring in the resultant imagery as the detector receives x-rays from different origination locations during the exposure time. The present technology allows for the incident x-rays during exposure to originate from approximately the same location from the perspective of the imaging target (that is, from the perspective of the imaging target, an effective focal spot of the x-ray emission appears to stationary during the exposure time). To do so, a cathode having an addressable array of electron-emitting sections is utilized.

As discussed in further detail below, by activating different or various portions of the electron-emitting sections on the cathode, the location, size, and shape of electron emission from a cathode can be controlled. By controlling the location, size, and shape of the electron emission from the cathode, a focal spot on the anode is also altered, thus allowing for control of the focal spot on the anode. Through control of the focal spot on the anode, an effective focal spot remains constant from the perspective of the breast even during movement of the x-ray source during an exposure in relation to the breast. Maintaining a constant effective focal spot during an exposure from the perspective of the breast allows for more accurate and clear imaging, among other benefits.

FIG. 1A depicts a breast tomosynthesis system 100. The tomosynthesis system 100 includes an x-ray tube 110, upper compression paddle 130, breast platform 135, an anti-scatter grid 160 and a detector 140. The x-ray source 110 includes a cathode 112, an anode 114 that is mounted on a shaft 116 and rotated by a motor 118, and a tube port 120. The x-ray source 110 is discussed below in further detail below with respect to FIGS. 2A-2G. The x-ray source 110 may also be operatively connected to a controller 162 for control of the x-ray source 110. A filter 122 may also be attached to the x-ray source or otherwise configured to filter the x-ray emission form the x-ray source 110.

The x-ray source 110 is attached to a rotating arm 105 that is configured to rotate about an axis parallel to the depicted longitudinal axis, both of which are parallel to the x-axis as shown in FIG. 1A. The rotating arm may be further connected to the controller 162 for control of the rotating arm and the x-ray source 110. During operation of the tomosynthesis system 100, a breast is held in place by the upper and lower compression paddles 130, 135 while radiation is being emitted from the x-ray source 110. The detector 140 may be stationary or may move during x-ray emission.

FIG. 1B depicts movement of an x-ray source 110 in the breast tomosynthesis system 100. Once the breast 106 is fixed in between the upper and lower compression paddles 130, 135, the rotating arm 105 rotates about the breast and the x-ray source 110 emits an x-ray emission 110 at multiple relative positions P1-P7 on an arc during the rotation, as shown in FIG. 1B. In examples the arc may span anywhere from 5 degrees to 360 degrees about the target (with 0 degrees and 360 degrees representing a horizontal line). In some applications, the arc spans between 15 degrees and 270 degrees. The arc length between positions may also be smaller or larger than depicted in FIG. 1B. That is, if the same number of positions are utilized on arcs having a total angle of 360 degrees and 135 degrees, the spacing between the positions in the 135 degree arc will be smaller. The motion of the x-ray source 110 is shown exaggerated for illustrative purposes. That is, during a tomosynthesis imaging procedure, the x-ray source 110 need not move across the complete range of motion depicted. In examples, the emissions may only occur between positions P1 and P4, or between positions P3 and P6, and so on. As noted above, the depicted positions P1 and P7 are relative positions that approximate locations where emission occurs for reference purposes only. For example, when the x-ray source reaches a position, such as P4, the x-ray source will begin emitting an x-ray emission 108 towards the breast 106. The x-ray emission 108 passes through the breast before reaching the detector 140. The emission of x-rays from the x-ray source 110 may be for a period of approximately 10 ms to 100 ms. During that period of emission, the x-ray source 110 continues to move relative to the compressed breast 106 and the detector 140. In traditional systems, blurring occurs due to the continuous movement during emission. In the present technology, however, the x-ray emission 108 can be altered during the movement to allow for the x-ray emission 108, as discussed further below. While only seven positions P1-P7 are shown in FIG. 1B, a greater or few number of positions may be utilized depending on the particular application.

Figure 2A:
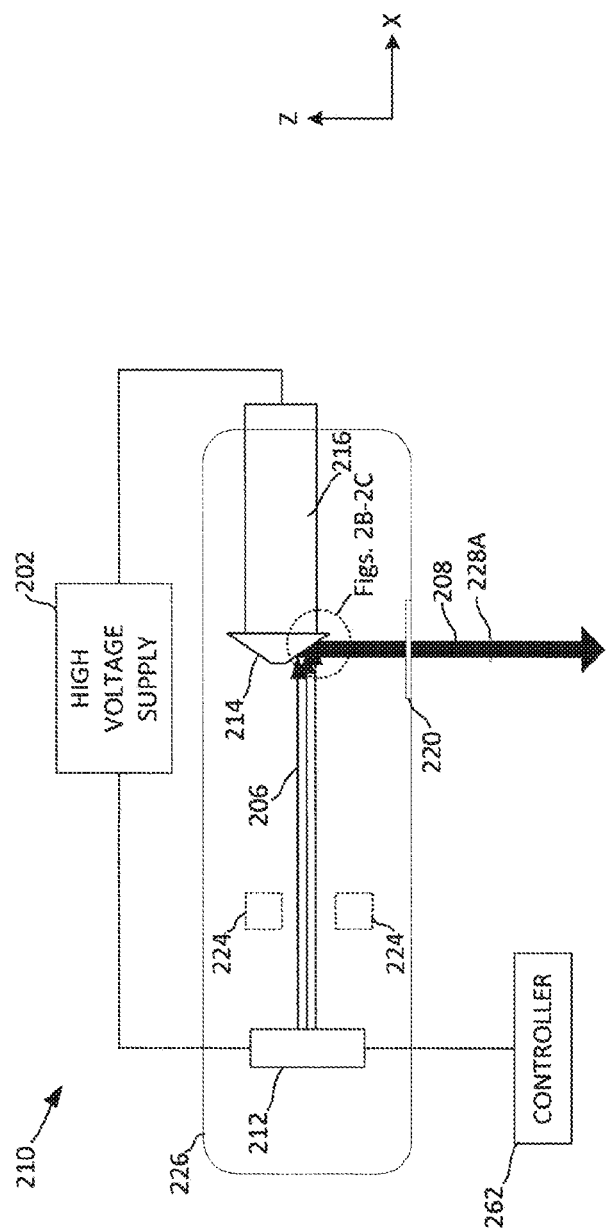
FIG. 2A depicts an example x-ray source.

FIG. 2A depicts a simplified example x-ray source 210. The example x-ray source 210 as shown includes a vacuum tube 226 housing a cathode 212 and an anode 214. The anode 214 may be attached to a shaft 216 and a motor (not shown) to allow for the anode 214 to be rotated during operation to prevent overheating of a target location on the anode 214. The cathode 212 and the anode 214 are also attached to high voltage power supply 202. The cathode 212 is connected to a controller 262 for control of the cathode 212 activation.

When the cathode 212 is activated, electrons are emitted from the cathode 212. A high voltage difference between the cathode 212 and the anode 214 causes the electrons to accelerate towards the anode 214 as an electron beam 206. Upon colliding and interacting with the anode 214, the electrons cause an x-rays to be emitted from the anode 214 in all directions. Some of the x-rays are emitted through the tube port 220, as indicated by x-ray emission 208, towards the imaging target, such as a breast. Optionally, the electrons may be focused to a particular spot on the anode 214 by a focusing device 224. The particular spot where electrons strike the anode 214 is referred to herein as the anode focal spot. The anode focal spot is represented by a two-dimensional area on the surface of the anode 214.

The size and location of the anode focal spot can be altered by focusing the electron beam 206 with a focusing device 224. The focusing device 224 may be a focus ring or focus cup that generates an electric or magnetic field that alters the direction of the electron beam 206 as it passes through or by the focusing device 224. In such an example, the focusing device is able to deflect the electron beam in both the y-direction and the z-direction, as shown in FIG. 2A. By deflecting the electron beam 206 in two-dimensions, the electron beam 206 can be focused to a smaller anode focal spot. For instance, if the cathode 212 emits electrons from a 3 mm×3 mm area, the focus-ring focusing device 224 may focus the electron beam 206 to a 0.3 mm×0.3 mm anode focal spot. In another example, the focusing device 224 may comprise two elements located on opposite sides of the electron beam 206. The two elements are capable of deflecting the electron beam in a single direction, such as the y-direction, by generating an electric or magnetic field. In such an example, if the cathode 212 emits electrons from a 3 mm×3 mm area, the two-element focusing device 224 may focus the electron beam 206 to a 0.3 mm×3 mm anode focal spot. The 3 mm dimension may then be shortened from the angle of the anode, as discussed below. Focusing devices may be arranged or configured to focus any size or shape of an electron beam coming from the cathode 212. The x-ray emission 208 generated from the anode focal spot in the direction of the breast through the tube port also defines a spot, referred to as an effective focal spot and discussed further below.

Figures 2B, 2C:
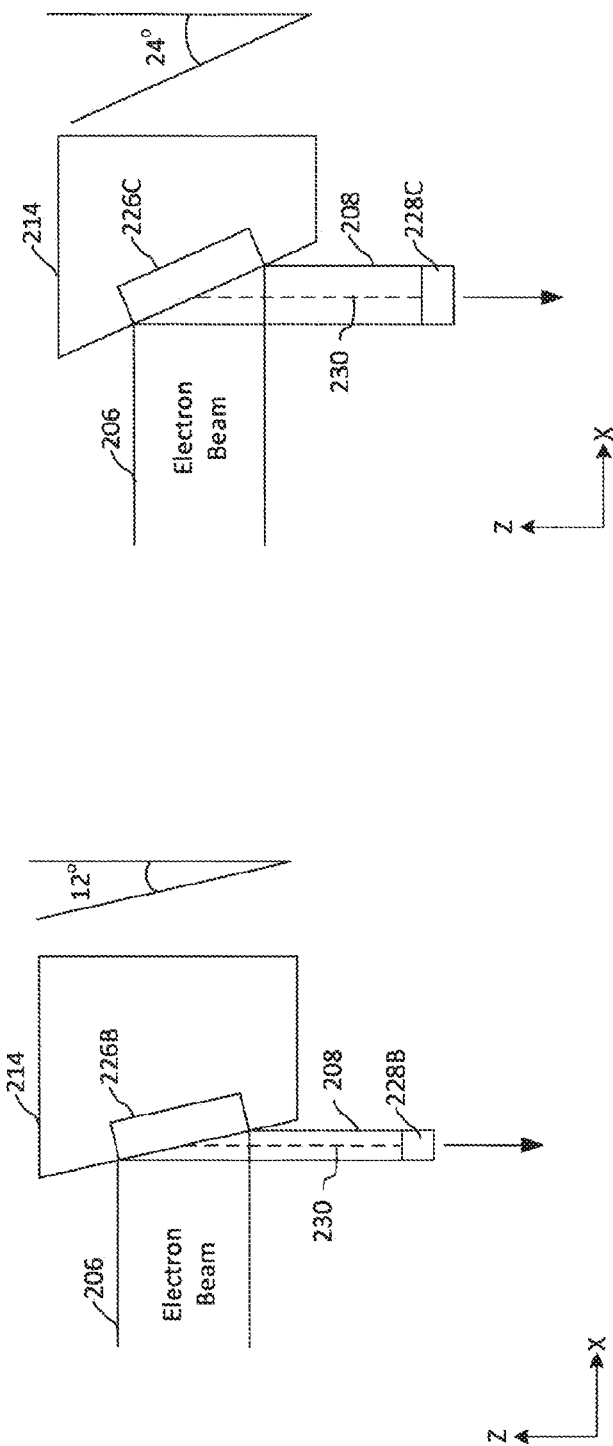
FIG. 2B depicts an anode having a first angle.
FIG. 2C depicts an anode having a second angle.

FIGS. 2B-2C depict two example of anodes having different angles. As shown in FIG. 2B, the electron beam 206 strikes the anode 214 in an area defining the anode focal spot 226B. The x-ray emission 208 from the anode focal spot 226B is emitted towards the target and has a cross-sectional area referred to as the effective focal spot 228B. The size of effective focal spot 226B affects the resolution of the final image produced by the tomosynthesis system 100, with smaller effective focal spots 226B generally allowing for higher resolution images. For instance, mammography systems may be designed to provide a 0.3 mm×0.3 mm effective focal spot for imaging, or a 0.1 mm×0.1 mm effective focal spot for high magnification images.

The size of the effective focal spot 228B is dependent on several factors, including the size of the anode focal spot 226B, and the angle of the face of the anode 214. By adjusting the angle of the face of the anode 214, one dimension (the x-dimension as depicted in FIGS. 2B-2C) of the effective focal spot 228B can be adjusted. As can be seen by comparing FIG. 2B with FIG. 2C, a smaller face angle for the anode results in a smaller effective focal spot 228B. For example, the face angle of the anode 214 in FIG. 2B is 12 degrees, whereas the face angle of the anode 214 in FIG. 2C is 24 degrees. As can be seen, the effective focal spot 228B is smaller than the effective focal spot 228C, despite being produced from the same anode focal spot (i.e., the same size electron beam). The x-ray emission 208 also has central line 230 indicating the central axis of the x-ray emission 208 directed towards the breast.

The size of the electron beam 206 is primarily based on the size of the active area of the cathode 212. The present technology utilizes a cathode 212 having an addressable array of electron-emitting sections to allow for controlled activation of discrete subsets of electron-emitting sections.

Figure 2D:
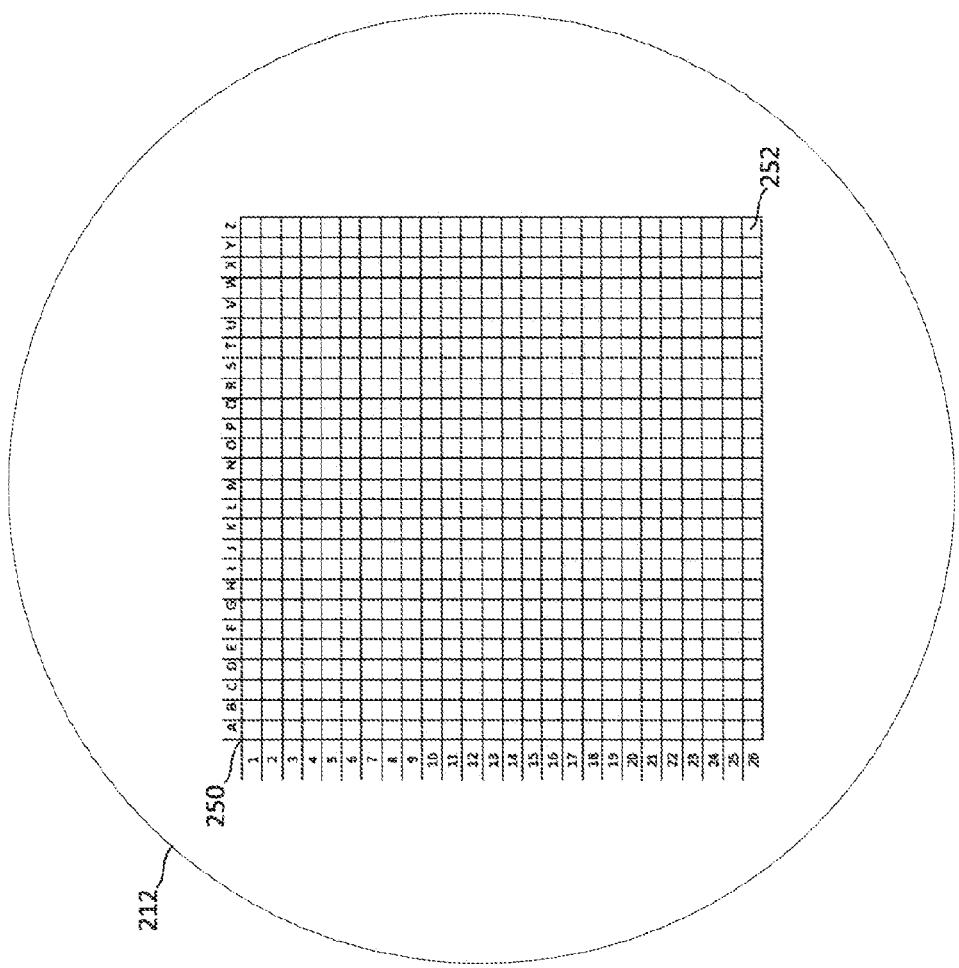
FIG. 2D depicts a cathode having an addressable array of electron-emitting sections.

FIG. 2D depicts an example of a cathode 212 having an addressable array 250 of electron-emitting sections 252. In the example cathode 212 depicted in FIG. 2D, each electron-emitting section 252 of the addressable array 250 may include a single electron emitter or many electron emitters. In some examples, each electron-emitting section 252 may be individually addressable so that each electron-emitting section 252 may be activated individually. Such an example provides a high amount of flexibility in creating a pattern and size of an electron emission area defined by the activated electron-emitting sections 252. In another example, each row (e.g., rows 1-26) may be individually addressable. In such an example, the electron emission sections 252 are activated in a row-by-row manner. For instance, columns J through P may be activated to create a rectangular electron emission area. The example addressable array 250 in FIG. 2D is arranged based on standard Cartesian coordinates, however, other arrangements of electron emission sections are also contemplated.

Figure 2E:
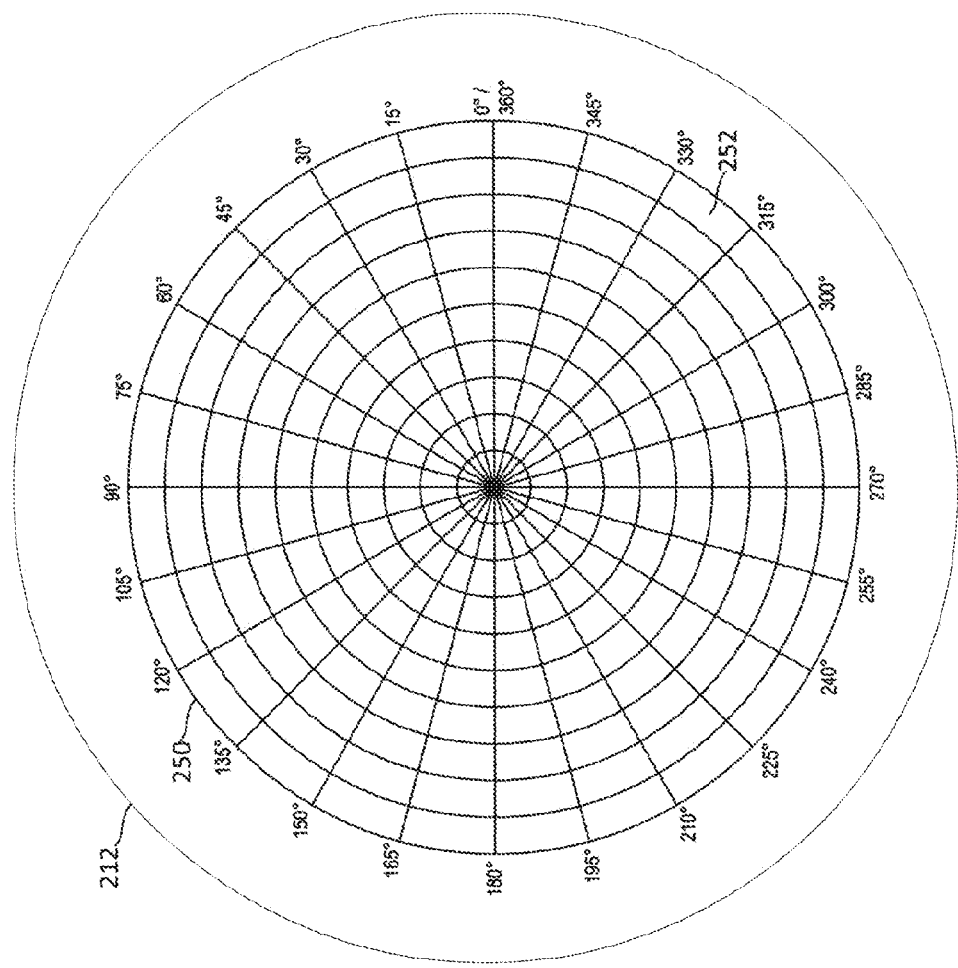
FIG. 2E depicts a cathode having an addressable array of electron-emitting sections.

FIG. 2E depicts another example of a cathode 212 having an addressable array 250 of electron-emitting sections 252. The cathode 212 depicted in FIG. 2E is similar to the cathode 212 depicted in FIG. 2D, except that the addressable array 250 is arranged based on polar coordinates rather than Cartesian coordinates. In the example cathode 212 depicted in FIG. 2E, the each electron-emitting section 252 of the addressable array 250 may include a single electron emitter or many electron emitters. In some examples, each electron-emitting section 252 may be individually addressable so that each electron-emitting section 252 may be activated individually such an example provides a high amount of flexibility in creating a pattern and size of an electron emission area defined by the activated electron-emitting sections 252. In another example, each angular section of the addressable array 250 may be individually addressable. For instance, all the electron-emitting sections 252 between angles 0 degrees to 15 degrees may be addressed similar to a row in the addressable array 250 depicted in FIG. 2D. In such an example, the electron emission sections 252 are activated angular section by angular section. Other arrangements based on different coordinate systems are also possible.

Figure 2F:
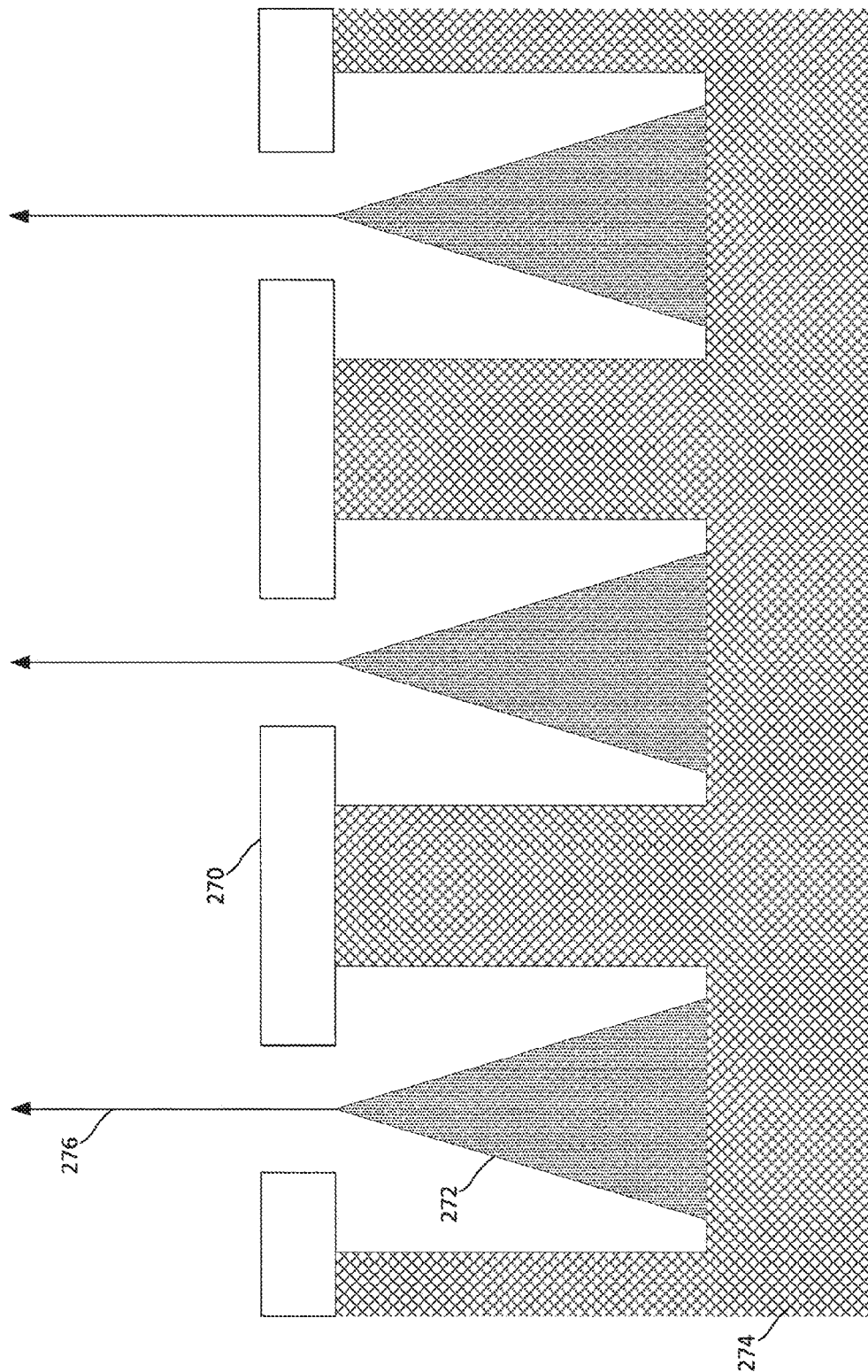
FIG. 2F depicts field-emission electron emitters on a cathode.

FIG. 2F depicts an example of electron emitters on a cathode 212. More specifically, FIG. 2F depicts an example of field-emission electron emitters. Field electronic emission is electron emission induced by an electrostatic field. This technology has been utilized in transistors, televisions, scanning electron microscopes, and other applications. The principles of field electron emission are generally known to a person of skill in the art. In the example depicted, each field-emission electron emitter includes a microtip 272 on a base 274. Above the microtip 272 is a gate layer 270. As a voltage difference is created between the gate layer 270 and the microtip 272, electrons 276 are emitted from the microtips 272. The field-emission electron emitters are affixed on the cathode 212 such that the electrons 276 project from the cathode 212 towards the anode 214 and are further accelerated based on the high-voltage difference between the cathode 212 and the anode 214. In embodiments, each of the microtips 272 can be individually addressed and activated. In some embodiments, rows or sections of the microtips 272 can be addressed and activated. In an example, the base 274 may be made of a silicon material, the microtips 272 may be made from a molybdenum or tungsten material, and the gate layer 270 may be made from a chromium, hafnium, niobium, or other conductive material. In other embodiments, the field-emission electron emitter may be a carbon-nanotube field emitter.

FIG. 2G depicts a portion of an addressable array 250 of field-emission electron emitters on a cathode (not shown). The addressable array 250 includes multiple field-emission emitters, which each include a microtip 272. Each microtip 272 is attached to a base 274. Spaced apart from the microtips 272 is a gate layer 272. The gate layer 272 defines a hole associated with each of the microtips 272 to allow for the emission of electrons when a selected electron emitter is activated. The base 274 may be divided into different sections by a base separator 275 that substantially prevents current from flowing from one side of the base separator 275 to the other side of the base separator 275. By including base separators 275, the voltage for the sectioned portions 276 of the base 274 can be individually controlled. In examples, controlling the voltage for each base section 276 also allows for control of the voltage on the corresponding microtip(s) 272 attached to the base section 276. For example, the base 274 may include base separators 275 to create rows of microtips 272. In such an example, a voltage may be applied to each row of microtips 272. In other examples, base separators 275 may be incorporated into the base 274 to separate each individual microtip 272. In such an example, a voltage may be applied to each discrete microtip 272.

The voltage to each base section 276 may be controlled through a set of base transistors 277. A base transistor 277 is connected to each base section 276 for which individual control and addressability is desired. In a configuration, the gates or bases of the base transistors 277 are connected to a controller 262 so that the controller 262 is able control each of the base transistors 277. Depending on the application, another end of the base transistor 277, such as the drain or collector, is connected to the base section 276 for which control is desired. The third end of the base transistor 277, such as the source or emitter, is connected to voltage source V1. In some examples, the voltage V1 is 0V or a ground with respect to a corresponding section of the gate layer 270.

The gate layer 270 may be sectioned similarly to the base 274 to allow for control of electron emission from each of the microtips 272 or a row of microtips 272. The gate layer 270 may include gate layer row separators 271 to separate the gate layer sections 278 above of a row of microtips 272. The gate layer 270 may also include gate layer column separators 273 to separate gate layer sections 278 above columns of microtips 272. The gate layer separators 271, 273 substantially prevent current from flowing from one side of the gate layer separator 271, 273 to the other side or the gate layer separator 271, 273. The gate layer separators 271, 273 may be arranged so that individual rows or columns of microtips 272 can be controlled and activated. The gate layer separators 271, 273 may also be arranged so that individual microtips 272 can be controlled and activated. The gate layer separators 271, 273 may also be arranged to encompass shared section of microtips 272.

The voltage to each gate layer section 278 may be controlled through a set of gate layer transistors 279. A gate layer transistor 279 is connected to each gate layer section 278 for which individual control and addressability is desired. For instance, there may be one gate layer transistor for each row of electron-emitting sections, each electron-emitting section, or each subset of electron-emitting sections, depending on the application and configuration. In a configuration, the gates or bases of the gate layer transistors 279 are connected to the controller 262 so that the controller is able to control each of the gate layer transistors 279. Depending on the application, another end of each gate layer transistor 279, such as the drain or collector, is connected to the gate layer section 278 for which control is desired. The third end of the base transistor, such as the source or emitter, is connected to voltage source V2. In some examples, the voltage V2 is approximately 100V greater than the corresponding base section voltage V1.

As discussed above, activation of a microtip 272 occurs when a voltage difference between the microtip 272 and the gate layer 270 is sufficiently large. By utilizing the various separators and transistors in the manner described relative to FIG. 2G, microtips 272 can be activated individually, by row, or by any other shaped section be controlling the voltage difference between a base section 276 and a corresponding gate layer section 278 directly above the respective base section 276. In some embodiments, only one of the base transistors 277 or the gate layer transistors 279 may be utilized. For example, the entire base may be grounded and the individual gate layer sections 278 are controlled via the gate layer transistors 279. In such an example, a voltage of 100V above ground may be selectively applied to each of the gate layer sections 278 by controlling the gate layer transistors 279. In another example, the entire gate layer 270 may be held at a voltage V2 and the respective voltages V1 of sections 276 of the base 274 may be individually controlled through the base transistors 277.

The gate layer 270, microtips 272, base 274, base transistors 277, and the gate layer transistors 279 may all be manufactured into a single integrated circuit or microchip that is incorporated into the cathode 212. The controller 262 may then control the microchip or integrated circuit through an interface designed to allow for a voltage to be discretely applied to each separated section 278 of the gate layer 270 and/or each separated section 276 of the base 274. Other potential control and manufacturing schemes are also contemplated and may be implemented.

Figure 2I:
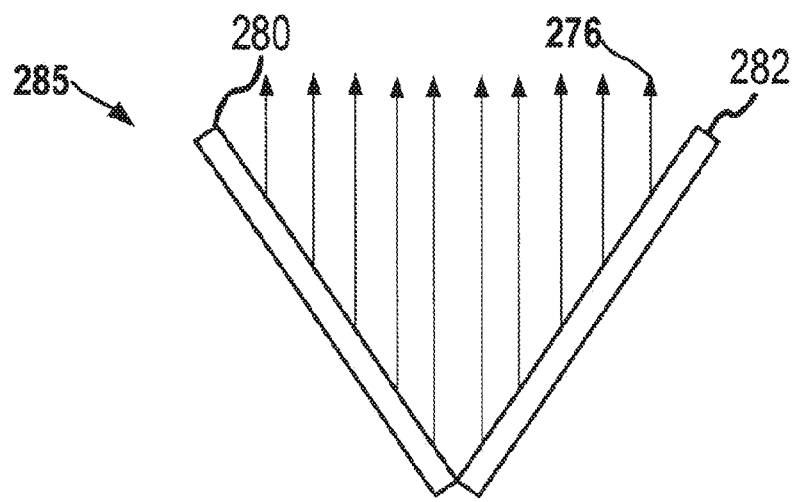
FIG. 2I depicts a side view of a v-shaped three-dimensional array.
Figure 2J:
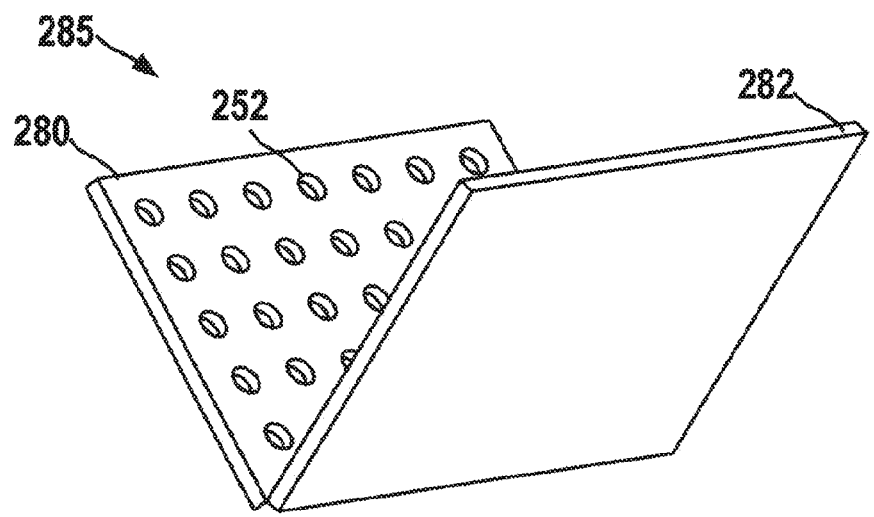
FIG. 2J depicts a perspective view of the v-shaped three-dimensional array

Three-dimensional (3D) addressable arrays may also be manufactured to increase the electron density emitting from a cathode having the 3D addressable array. For example, the addressable arrays may be arranged to form a parabolic or cone shape to emit additional electrons than what would be possible with a single flat surface. As compared to two-dimensional addressable array, a 3D addressable array has a distribution of electron-emitting sections across the x-direction, the y-direction, and the z-direction when incorporated into a cathode of an x-ray tube, such as the x-ray tube depicted in FIG. 2A. Such a 3D addressable array may be manufactured as a single component or generated from multiple planar surfaces, among other potential manufacturing methods. FIG. 2H depicts two cathode plates 280, 282 having addressable arrays 250 of electron-emitting sections 252. The electron-emitting sections 252 may be field emission electron emitting sections and may be individually addressable, as discussed above with reference to FIGS. 2F-2G. The cathode plates 280, 282 may be combined to form a v-shaped 3D addressable array for use in a cathode, as shown in FIGS. 2I and 2J. FIG. 2I depicts a side view of the v-shaped 3D addressable array 285. Each of the electron-emitting sections 252 of the cathode plates 280, 282 may emit electrons 276. As can be seen from FIG. 2I, by arranging the cathode plates in a v-shape, the maximum electron density that can be emitted from the v-shaped addressable array 285 is greater than the maximum electron density than may be emitted from a single planar addressable array. While only two cathode plates 280, 282 have been depicted herein to create the 3D addressable array 285, additional smaller cathode plates may also be used to further approximate a parabolic or u-shape or v-shape for the 3D addressable array 285. For example, each row of electron-emitting sections 252 may be manufactured on a discrete cathode plate, and each cathode plate may be connected at an appropriate angle to each other cathode plate to approximate a parabolic shape.

Figure 2K:
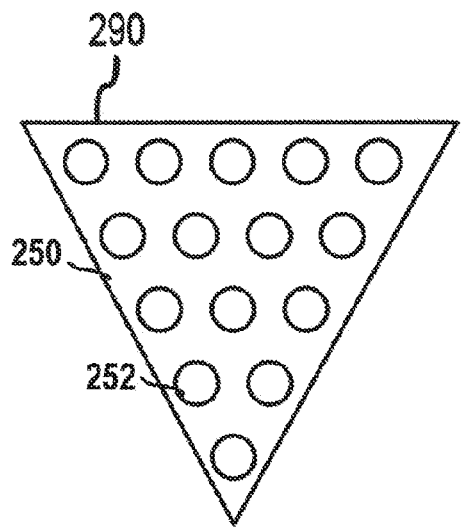
FIG. 2K depicts a set of cathode plates having addressable arrays of electron-emitting sections.
Figure 2K:
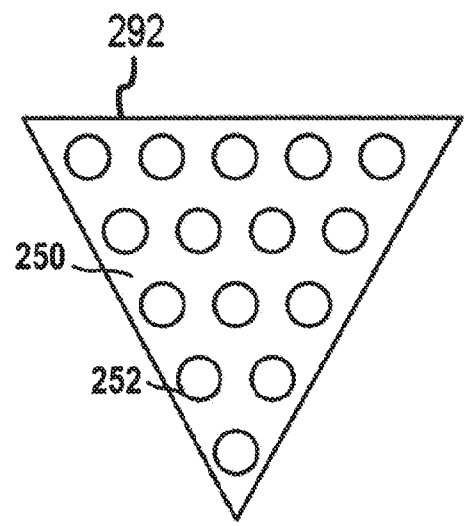
Figure 2K:
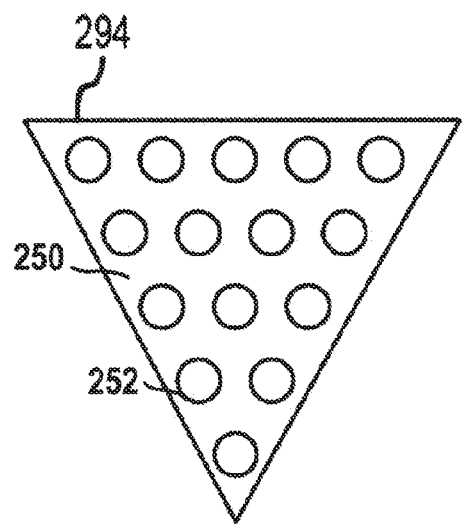
Figure 2K:
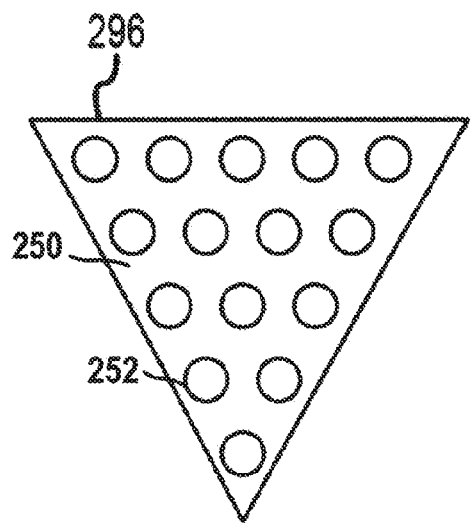
Figure 2L:
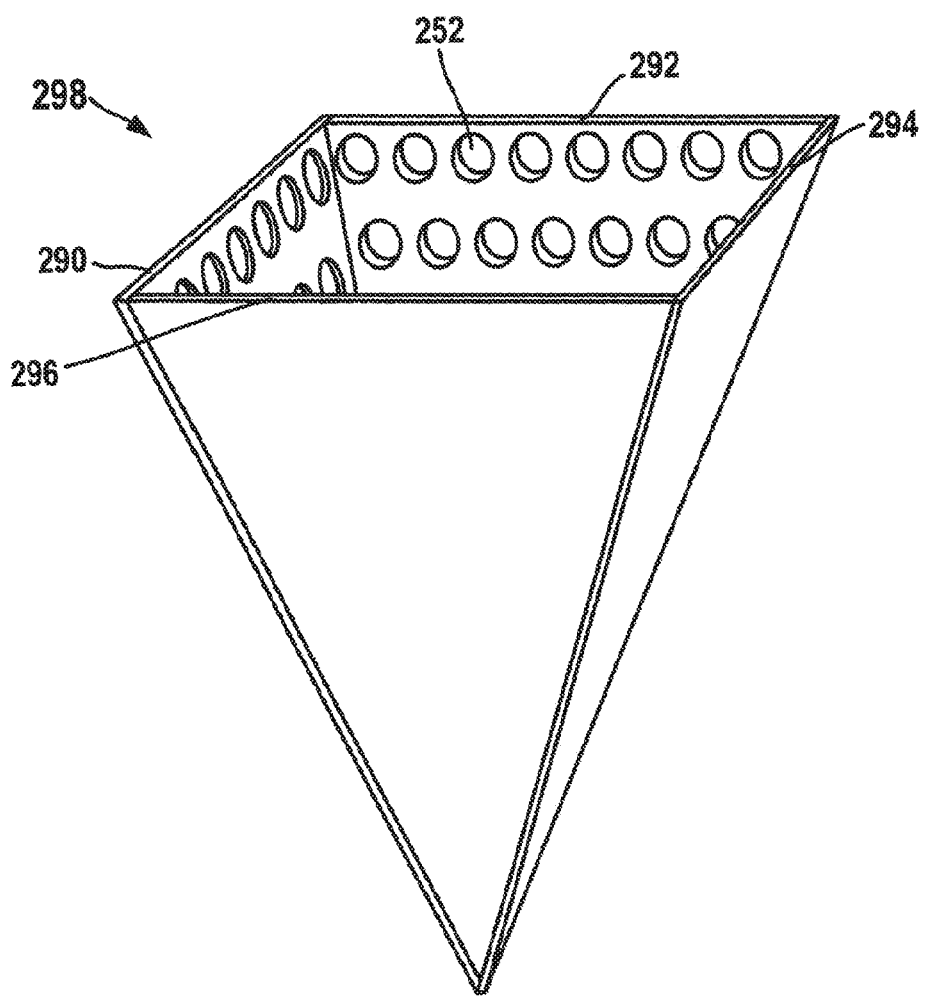
FIG. 2L depicts a perspective view of a pyramidal three-dimensional addressable array.

Multiple cathode plates may also be utilized to approximate a cone shape or a hollow pyramid shape for a 3D addressable array. FIG. 2K depicts a set of cathode plates 290, 292, 294, 296 having addressable arrays 250 of electron-emitting sections 252. Similar to the electron-emitting sections 252 of cathode plates 280, 282 depicted in FIGS. 2H-J, the electron-emitting sections 252 in cathode plates 290, 292, 294, 296 may be field emission electron emitting sections and may be individually addressable, as discussed above with reference to FIGS. 2F-2G. The set of cathode plates 290, 292, 294, 296 may be used to manufacture a pyramidal 3D addressable array 398, shown in FIG. 2L. FIG. 2L depicts a perspective view of the pyramidal 3D addressable array 398 manufactured from the set of cathode plates 290, 292, 294, 296. By using a pyramidal 3D addressable array 298 in a cathode, a higher electron density may be generated than can be generated from a single planar surface of electron-emitting sections 252 or a v-shaped 3D addressable array. While only four cathode plates 290, 292, 294, 296 have been depicted herein to create the 3D addressable array 298, additional smaller cathode plates may also be used to further approximate a conical shape for the 3D addressable array 298. For example, each row of electron-emitting sections 252 may be manufactured on a discrete cathode plate, and each cathode plate may be connected at an appropriate angle to each other cathode plate to approximate a parabolic shape. Further, while the term cathode plate has been used herein to describe the planar surfaces used in manufacturing the 3D addressable arrays, one having skill in the art will appreciate that the concept of a cathode plate is not limited solely to a plate structure. Any surfaces or structures including an addressable array of electron emitting sections may be used as, and considered to be a cathode plate or its equivalent.

Operation of a 3D addressable array, such as the v-shaped 3D addressable array 285 or the pyramidal 3D addressable array, may be similar to the control of the addressable array 250 as discussed above with reference to FIG. 2G. For instance, somewhat linear control of the electron-emitting sections 252 may still be accomplished, however, three-dimensional control of the electron-emitting sections 252 may also be accomplished. By controlling the electron-emitting sections 252 in three dimensions, the size and shape of the focal spot may be further modified. In an example of a cone-shaped 3D addressable array or a pyramidal 3D addressable array 298, two of the cathode plates, such as cathode plates 290, 294 may be used to move the focal spot linearly, while the other two cathode plates 292, 296 may be used to control or direct the electrons being emitted by the cathode plates 290, 294. For instance, electrons emitted from one cathode plate will interact with electrons emitted from other cathode plates. By controlling the addressable arrays, such interactions may be further manipulated or utilized in generating a desired focal spot. As such, a first set of electron-emitting sections may be used for shifting the focal spot, and a second set of electron-emitting sections may be used to modify the electrons emitted from those electron-emitting sections.

Figure 3A:
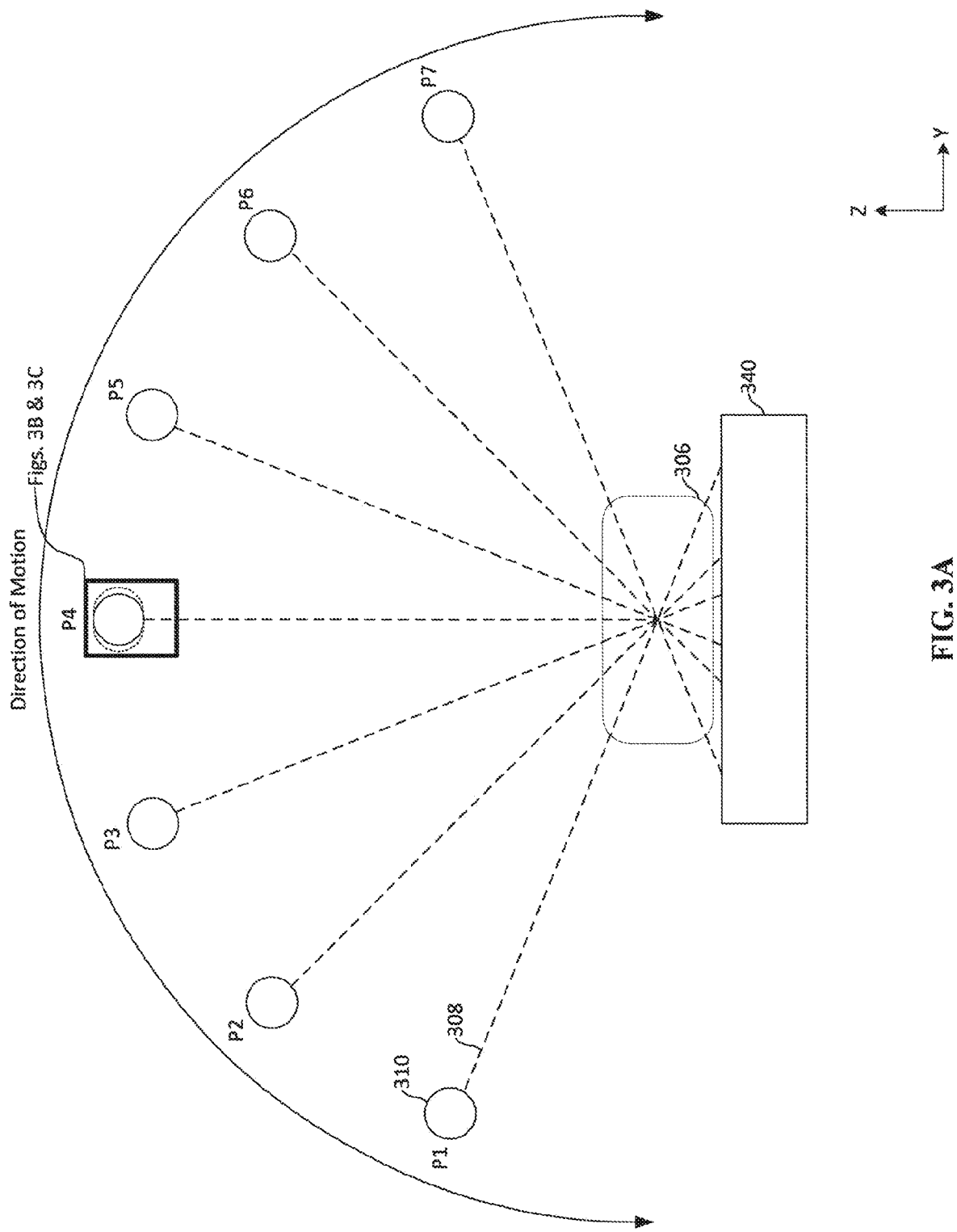
FIG. 3A depicts movement of an x-ray source in a breast tomosynthesis system.
Figure 3B:
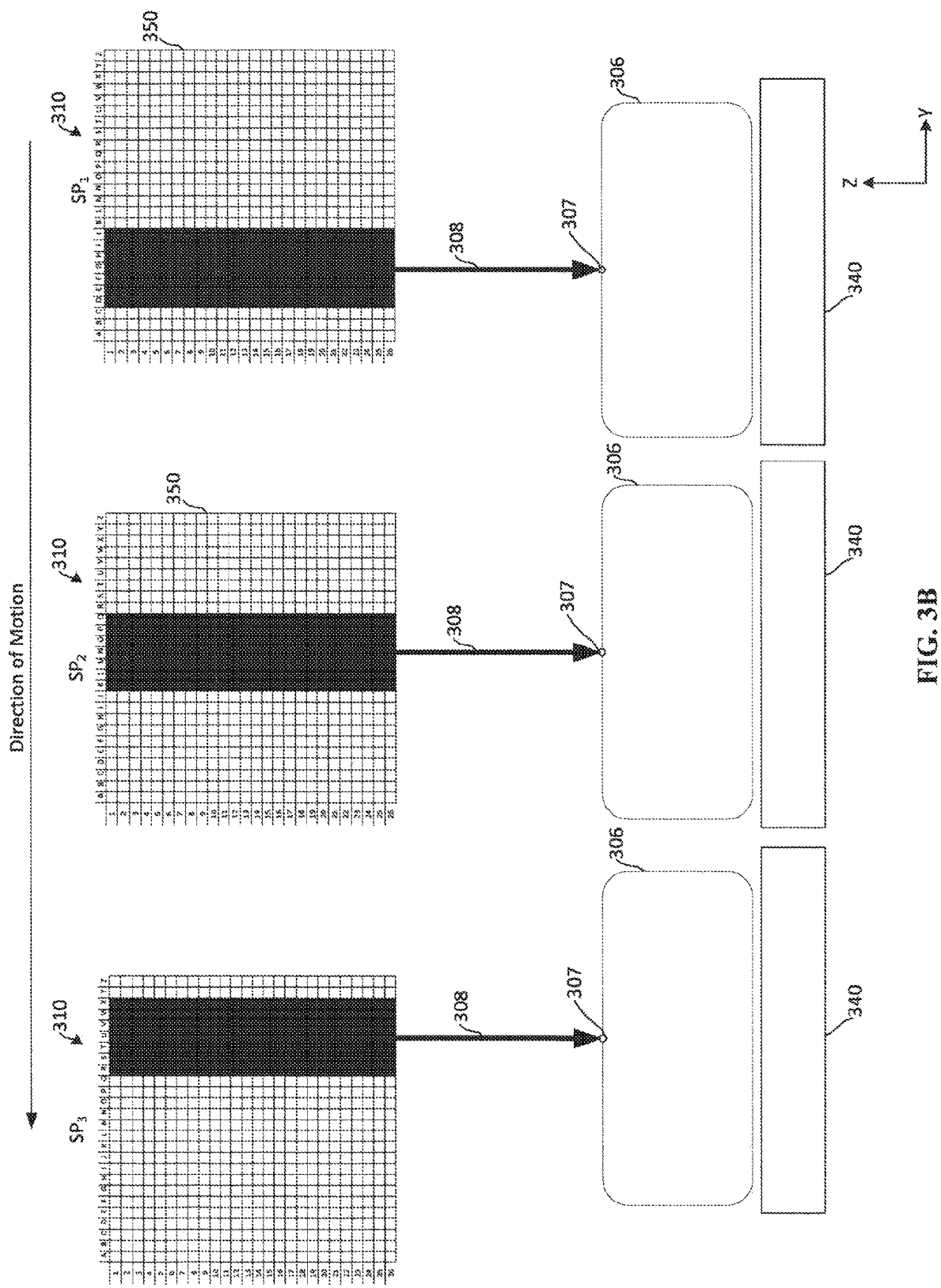
FIG. 3B depicts an example of activating electron-emitting sections during movement of the x-ray source.
Figure 3C:
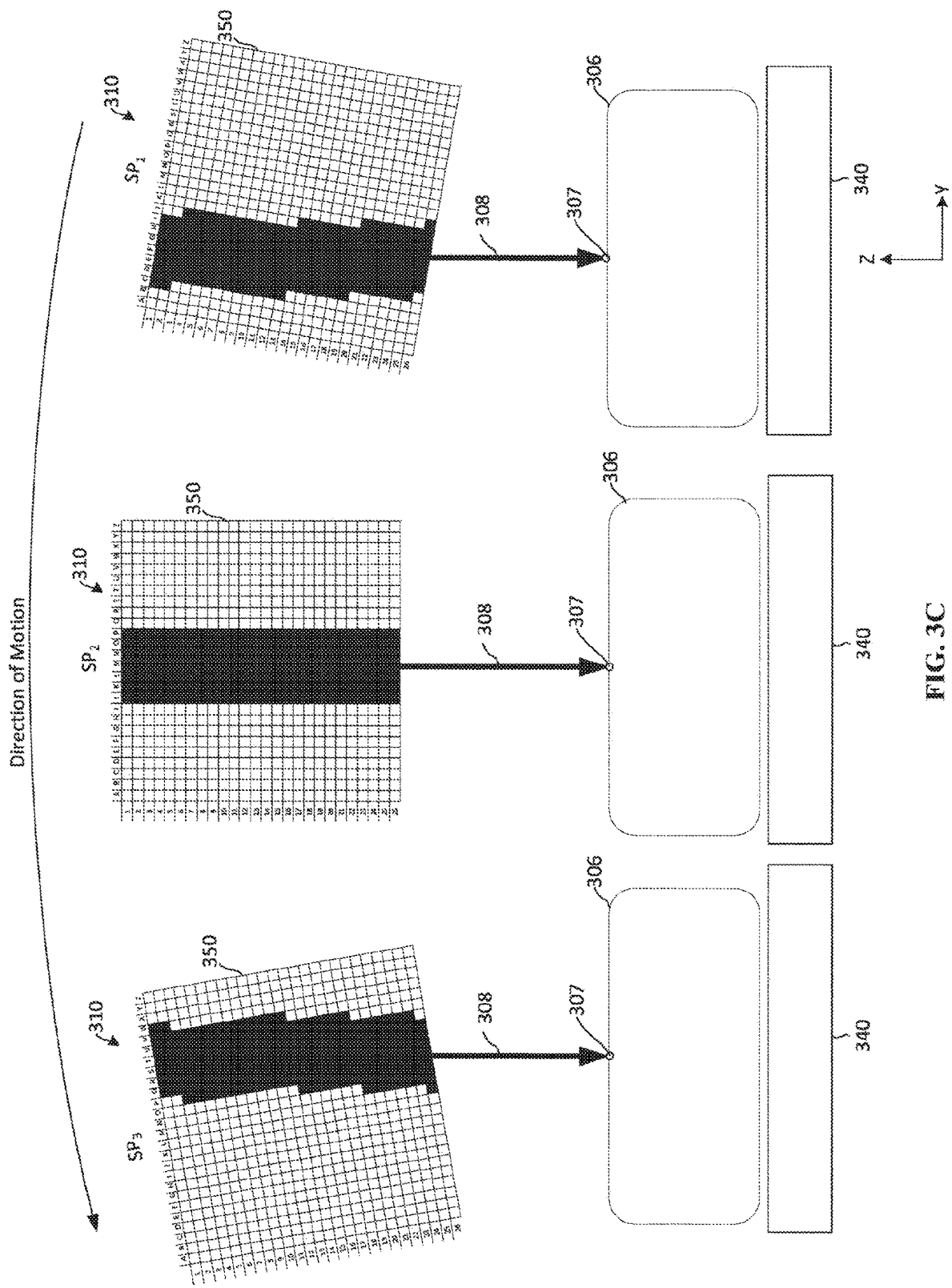
FIG. 3C depicts an example of activating electron-emitting sections during movement of the x-ray source.

FIG. 3A depicts movement of an x-ray source 310 in the breast tomosynthesis system 300. The movement of the x-ray source 310 is substantially the same as the movement of the x-ray source 310 discussed above with reference to FIG. 1B. The x-ray source 310 rotates relative to the breast 306 and the x-ray source 310 emits an x-ray emission 308 at multiple positions P1-P7 during the rotation. For example, when the x-ray source reaches a position, such as position P4, the x-ray source will begin emitting an x-ray emission 308 towards the breast 306. The x-ray emission 308 passes through the breast before reaching the detector 340. The emission of x-rays from the x-ray source 310 for a period of approximately 10 ms to 100 ms. During that period of emission, the x-ray source 310 continues to move relative to the breast 306 and the detector 340, as shown by the dashed circles and box surrounding the x-ray source 310 at P4. In traditional systems, from the perspective of the breast 306, an effective focal spot appears to move or grow in size during emission while the x-ray source 310 is moving. In the present technology, different subsets of electron-emitting sections on the cathode can be activated during the movement of the x-ray source 310 to compensate for the movement of the x-ray source 310 in order to make the effective focal spot appear stationary from the perspective of the breast. For example, if the x-ray source 310 is moving in a counter-clockwise direction, subsets of electron-emitting sections are consecutively activated in the clockwise direction. FIGS. 3B and 3C depict two examples of activating subsets of electron-emitting sections to compensate for movement of the x-ray source 310 around position P4.

FIG. 3B depicts an example of activating electron-emitting sections during movement of the x-ray source 310. The addressable array 350 on the cathode of an x-ray source 350 is depicted in FIGS. 3B-3C. As will be appreciated, upon activation of electron-emitting sections in the addressable array 350, electrons emitting from the active sections accelerate to an anode (not shown) and x-rays are generated from the anode, thus causing an x-ray emission 308 to be directed towards the breast 306, as discussed above with reference to FIGS. 2A-2G. As x-ray source 310 moves through a position, such as position P4 in FIG. 3A, the x-ray source 310 emits an x-ray emission 308. While emitting x-rays, the x-ray source 310 passes through multiple sub-positions SP1-SP3. FIG. 3B depicts the x-ray source 310 moving in a counter-clockwise direction through sub-positions SP1-SP3. In the example depicted in FIG. 3B, the movement through the sub-positions SP1-SP3 is approximated to be linear motion, although the actual motion of the x-ray source may be rotational around the x-axis (e.g., as defined by the breast). When the x-ray source 310 is in sub-position SP1, a first subset of electron-emitting sections of the addressable array 350 is activated. The subset of electron-emitting sections at each sub-position is depicted by shading in the addressable array 350. For instance, at sub-position SP1, rows D-J are included in a first subset of electron-emitting sections. At sub-position SP1, activation of the first subset of electron-emitting sections causes an x-ray emission 308 to be emitted from the x-ray-source 310 towards a single location 307 on the breast 306. For example, the center line of the x-ray emission 308 is directed at a single location 307 on the breast 306.

As the x-ray source 310 moves from sub-position SP1 to SP2, a second subset of electron-emitting sections of the addressable array 350 is activated. As shown in FIG. 3B, the second subset of electron-emitting sections includes rows K-Q of the addressable array 350. By shifting the active electron-emitting sections from the first subset to the second subset of electron-emitting sections, the x-ray emission 308 from the x-ray source 310 continues to be directed at the same single location 307 on the breast 306. More specifically, the center line of the x-ray emission 308 continues to be directed to the single location 307 on the breast 306. Also, from the perspective of the breast 306 and the detector 340, the effective focal spot of the x-ray emission remains substantially the same shape, size, and location as the x-ray source moves from sub-position SP1 to SP2.

As the x-ray source 310 moves from sub-position SP2 to SP3, a third subset of electron-emitting sections of the addressable array 350 is activated. As shown in FIG. 3B, the third subset of electron-emitting sections includes rows R-X of the addressable array 350. By shifting the active electron-emitting sections from the second subset to the third subset of electron-emitting sections, the x-ray emission 308 from the x-ray source 310 continues to be directed at the same single location 307 on the breast 306. More specifically, the center line of the x-ray emission 308 continues to be directed to the single location 307 on the breast 306. Also, from the perspective of the breast 306 and the detector 340, the effective focal spot of the x-ray emission remains substantially the same shape, size, and location as the x-ray source moves from sub-position SP1 to SP2 and from SP2 to SP3.

By utilizing a linear approximation of the rotational motion of the x-ray source 310, activation of whole rows of the addressable array 250 is performed, as shown in FIG. 3B. In applications requiring further precision, however, the linear approximation may not be sufficient. FIG. 3C depicts an example of activating electron-emitting sections during movement of the x-ray source 310 that accounts for rotational aspects of the x-ray source 310. As x-ray source 310 moves through a position, such as position P4, the x-ray source 310 emits an x-ray emission 308. FIG. 3C depicts the x-ray source 310 moving in a counter-clockwise direction through sub-positions SP-SP3. When the x-ray source 310 is in sub-position SP1, a first subset of electron-emitting sections of the addressable array 350 is activated. For instance, at sub-position SP1, portions of electron-emitting sections from rows C-M of the addressable array 350 are a activated. In contrast to the example depicted in FIG. 3B, some of the rows are not fully activated so as to account for the rotational movement of the x-ray source 310. At sub-position SP1, activation of the first subset of electron-emitting sections causes an x-ray emission 308 to be emitted from the x-ray-source towards a single location 307 on the breast 306. For example, the center line of the x-ray emission 308 is directed at a single location 307 on the breast 306.

As the x-ray source 310 moves from sub-position SP1 to SP2, a second subset of electron-emitting sections of the addressable array 350 is activated. As shown in FIG. 3B, the second subset of electron-emitting sections includes electron-emitting sections rows J-P of the addressable array 350. By shifting the active electron-emitting sections from the first subset to the second subset of electron-emitting sections, the x-ray emission 308 from the x-ray source 310 continues to be directed at the same single location 307 on the breast 306. More specifically, the center line of the x-ray emission 308 continues to be directed to the single location 307 on the breast 306. Also, from the perspective of the breast 306 and the detector 340, the effective focal spot of the x-ray emission remains substantially the same shape, size, and location as the x-ray source 310 moves from sub-position SP1 to SP2.

As the x-ray source 310 moves from sub-position SP2 to SP3, a third subset of electron-emitting sections of the addressable array 350 is activated. As shown in FIG. 3B, the third subset of electron-emitting sections includes electron-emitting sections from rows M-W of the addressable array 350. In the example depicted in FIG. 3C, the third subset includes electron-emitting sections from the second subset, and the first subset includes electron-emitting sections from the first subset. In other examples, the subsets of electron-emitting sections may not overlap. By shifting the active electron-emitting sections from the second subset to the third subset of electron-emitting sections, the x-ray emission 308 from the x-ray source 310 continues to be directed at the same single location 307 on the breast 306. More specifically, the center line of the x-ray emission 308 continues to be directed to the single location 307 on the breast 306. Also, from the perspective of the breast 306 and the detector 340, the effective focal spot of the x-ray emission remains substantially the same shape, size, and location as the x-ray source 310 moves from sub-position SP1 to SP2 and from SP2 to SP3. Other subsets of electron-emitting sections may also be utilized to cause the center line of the x-ray emission 308 to remain substantially directed towards the single location 307. For example, while the subsets of the electron-emitting sections shown in FIGS. 3B-3C are shown as substantially rectangular, the geometry of the shape of the subsets of electron-emitting sections may vary depending on the application. For instance, depending on the emission characteristics, the gap between the anode and cathode, anode angle, and other anode-cathode alignment geometries, the shape of the electron-emitting sections may be approximately a triangle, rectangle, other regular or irregular polygon, a circle, an oval, or any other curved or irregular curved shape. These shapes may need further fine optimization to control the desired focal spot shape (e.g., turning on or off individual active electron emitting elements). Additionally as the x-ray source 310 is moved as described herein, the shape of the active subset of electron-emitting sections may utilize dynamic real-time adaptation to control the effective focal spot and x-ray geometries.

Figure 4:
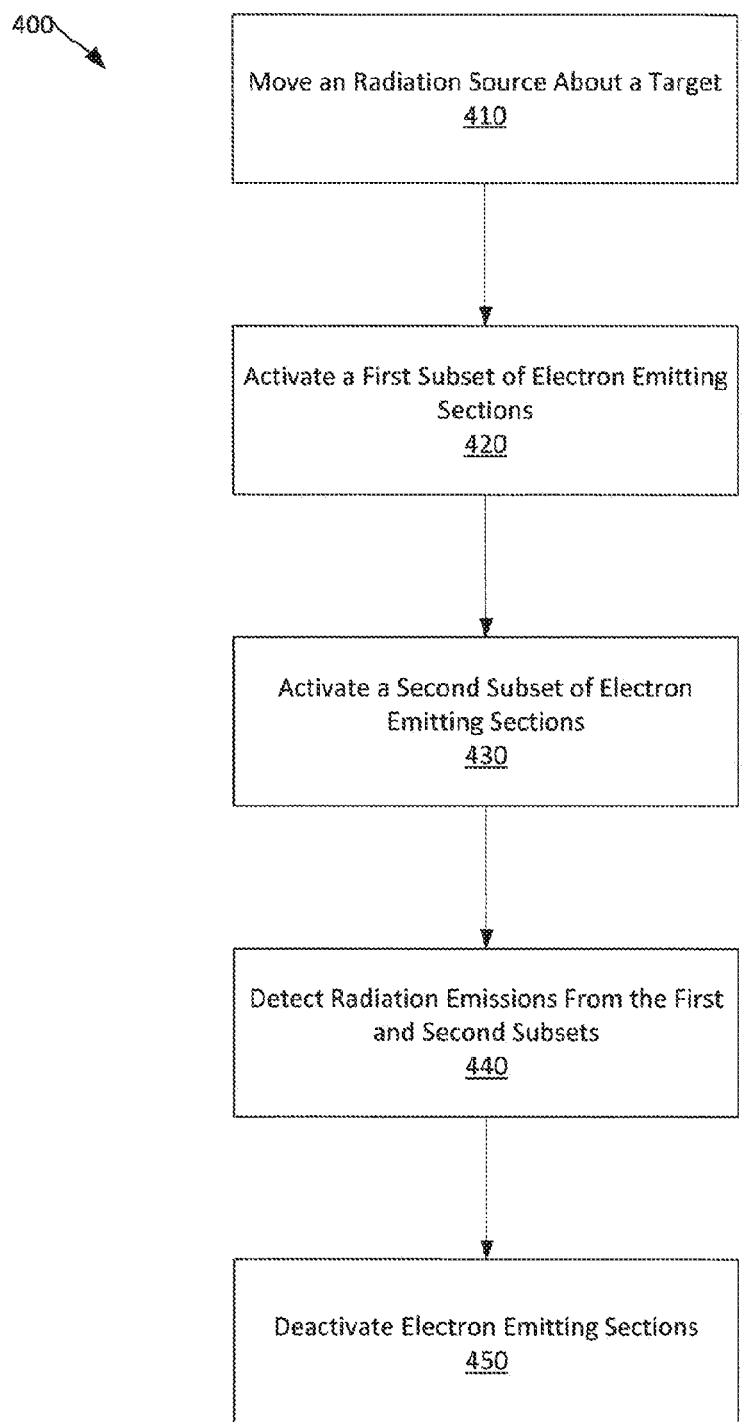
FIG. 4 depicts a method of using a tomosynthesis system for imaging.

FIG. 4 depicts a method 400 of using a tomosynthesis system for imaging. At operation 410, a radiation source, such as an x-ray source, is moved relative to a target, such as a breast. As the radiation source is moving relative to the target, a first subset of electron-emitting sections in an addressable array on a cathode of the radiation source is activated at operation 410. Activation of the first subset of electron-emitting sections causes an x-ray emission to be directed to a single location on the target, such as the breast. At operation 420, while the radiation source continues moving, a second subset of electron-emitting sections of the addressable array on the cathode is activated to compensate for movement of the radiation source from a first position to a second position. Activation of the second subset of electron-emitting sections causes the x-ray emission to continue to be directed to the single location on the target. In embodiments, activation of the second subset of electron-emitting sections causes the effective focal spot of the x-ray emission to appear stationary from the perspective of the target. From the perspective of the target, the effective focal spot may also appear to remain unchanging in size, shape, and position during the x-ray emission from the first and second subset of electron-emitting sections. As the radiation source moves through the first position and the second position, the radiation emitting from the radiation source is detected at operation 440. After the radiation source has emitted a sufficient amount of time for imaging, such as 10 ms to 100 ms, the electron-emitting sections are deactivated at operation 450. While only two subsets of electron-emitting sections are discussed with reference to method 400, many more subsets may be utilized to more precisely compensate for movement of the radiation source while emitting radiation. Also, when shifting subsets of electron-emitting sections, the shift may be to another subset of electron-emitting sections in either the z-direction, the y-direction, or both directions with respect to the coordinate system depicted in the figures. As will be appreciated, shifting from one subset of electron-emitting sections to another set of electron emitting sections of the cathode will cause a shift in the anode focal spot.

While primarily discussed herein as activating electron-emitting subsets to compensate for movement of an x-ray source, activating electron-emitting subsets may also be performed for other purposes. For instance, activating electron-emitting subsets may be performed on a stationary radiation source to make the x-ray emission appear to be moving from the perspective of the breast.

Figure 5:
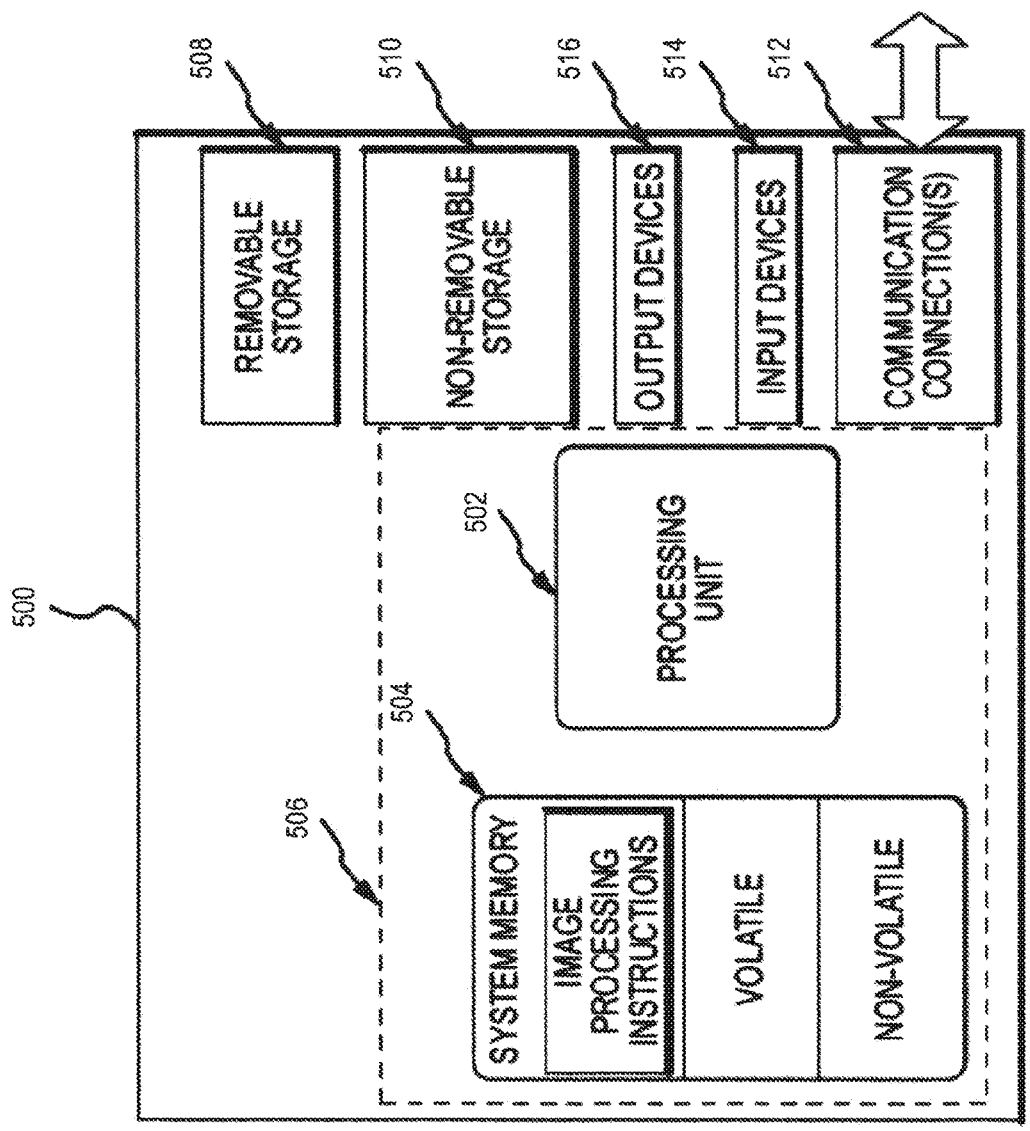
FIG. 5 depicts illustrates one example of a suitable operating environment in which one or more of the present examples can be implemented.

FIG. 5 illustrates one example of a suitable operating environment 500 in which one or more of the present embodiments can be implemented. This operating environment may be incorporated directly into a tomosynthesis system, or may be incorporated into a computer system discrete from, but used to control, a tomosynthesis system such as described herein, such as the controller. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 500 typically includes at least one processing unit 502 and memory 504. Depending on the exact configuration and type of computing device, memory 504 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 5 by dashed line 506. Further, environment 500 can also include storage devices (removable, 508, and/or non-removable, 510) including, but not limited to, magnetic or optical disks or tape. Similarly, environment 500 can also have input device(s) 514 such as touch screens, keyboard, mouse, pen, voice input, etc., and/or output device(s) 516 such as a display, speakers, printer, etc. Also included in the environment can be one or more communication connections 512, such as LAN, WAN, point to point, Bluetooth, RF, etc.

Operating environment 500 typically includes at least some form of computer readable media. Computer readable media can be any available media that can be accessed by processing unit 502 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 500 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 500 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 500 is part of a network that stores data in remote storage media for use by the computer system 500.

Figure 6:
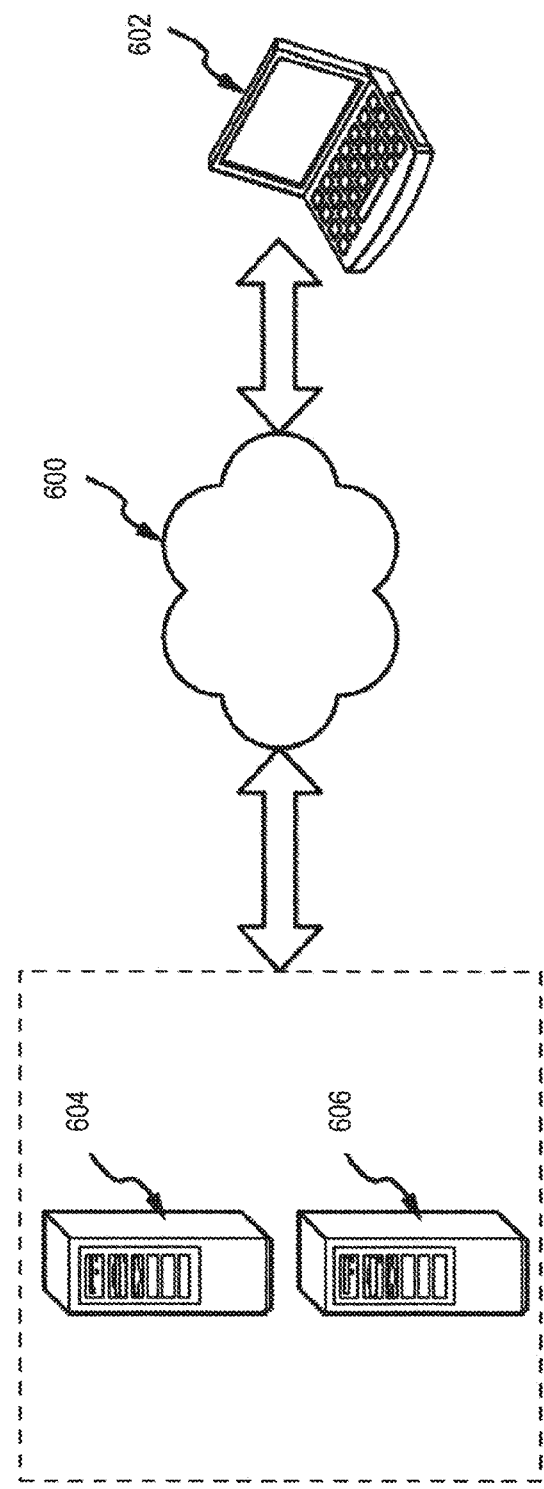
FIG. 6 is an embodiment of a network in which the various systems and methods disclosed herein may operate.

FIG. 6 is an embodiment of a network 600 in which the various systems and methods disclosed herein may operate. In embodiments, a client device, such as client device 602, may communicate with one or more servers, such as servers 604 and 606, via a network 608. In embodiments, a client device may be a laptop, a personal computer, a smart phone, a PDA, a netbook, or any other type of computing device, such as the computing device in FIG. 5. In embodiments, servers 604 and 606 may also be any type of computing device, such as the computing device illustrated in FIG. 5. Network 608 may be any type of network capable of facilitating communications between the client device and one or more servers 604 and 606. For example, the x-rays detected by the detector may be recognized locally in the tomosynthesis system and communicated to another computing device(s) for further processing, such as an image acquisition workstation. Examples of such networks include, but are not limited to, LANs, WANs, cellular networks, and/or the Internet.

In embodiments, the various systems and methods disclosed herein may be performed by one or more server devices. For example, in one embodiment, a single server, such as server 604 may be employed to perform the systems and methods disclosed herein, such as the method for utilizing the tomosynthesis system. Client device 602 may interact with server 604 via network 608. In further embodiments, the client device 602 may also perform functionality disclosed herein, such as scanning and image processing, which can then be provided to servers 604 and/or 606.

In alternate embodiments, the methods and systems disclosed herein may be performed using a distributed computing network, or a cloud network. In such embodiments, the methods and systems disclosed herein may be performed by two or more servers, such as servers 604 and 606. Although a particular network embodiment is disclosed herein, one of skill in the art will appreciate that the systems and methods disclosed herein may be performed using other types of networks and/or network configurations.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. Embodiments according to the invention may also combine elements or components of those that are disclosed in general but not expressly exemplified in combination, unless otherwise stated herein. The scope of the technology is defined by the following claims and any equivalents therein.

What is claimed is:

1. A system for radiographic imaging, the system comprising:
    a rotating arm configured to rotate relative to a target tissue;
    a radiation source attached to the rotating arm, the radiation source comprising a cathode and an anode, wherein the cathode comprises an array of electron-emitting sections; and
    a controller operatively connected to the cathode, the controller configured to activate a first subset of the array of electron-emitting sections when the radiation source is located in a first position relative to the target, and activate a second subset of the array of electron-emitting sections when the radiation source is located in a second position relative to the target, wherein the second subset of electron-emitting sections are selected to compensate for movement from the first position to the second position in order to make a focal spot appear stationary from the perspective of the target.

2. The system of claim 1, wherein the rotating arm moves in a first direction and the second subset of the array of electron-emitting sections includes electron-emitting sections spaced apart from the first subset of the array of electron-emitting sections in a direction opposite the first direction.

3. The system of claim 1, wherein each electron-emitting section includes at least one field emission emitter.

4. The system of claim 3, wherein each electron-emitting section includes at least one carbon-nanotube emitter.

5. The system of claim 1, wherein the first subset of electron-emitting sections and the second subset of electron-emitting sections are individually addressable by the controller.

6. The system of claim 1, wherein the array comprises multiple rows of electron-emitting sections, wherein each row is individually addressable by the controller.

7. The system of claim 6, wherein each row includes a gate portion and an emitter portion, the gate portion connected to a transistor connected to the controller.

8. The system of claim 1, wherein each electron-emitting section is individually addressable by the controller.

9. The system of claim 8, wherein each electron-emitting section includes a gate portion and an emitter portion, the gate portion connected to a transistor connected to the controller.

10. The system of claim 1, wherein the radiation source is configured to emit radiation to a single location on the target as the radiation source moves from the first position and the second position.

11. A method for radiographic imaging, the method comprising:
    moving a radiation source relative to a target from a first position to a second position while emitting radiation from the radiation source to a location of the target, the radiation source including an array of electron-emitting sections;
    while moving the radiation source from the first position to the second position, activating a first subset of the electron-emitting sections at the first position and activating a second subset of electron-emitting sections at the second position, wherein the second subset of electron-emitting sections are selected to compensate for movement from the first position to the second position in order to make a focal spot appear stationary from the perspective of the target; and detecting the emitted radiation.

12. The method of claim 11, wherein the second subset of the array of electron-emitting sections includes electron-emitting sections from the first subset of the array of electron-emitting sections.

13. The method of claim 11, wherein each electron-emitting section includes at least one field emission emitter.

14. The method of claim 11, wherein each electron-emitting section includes at least one carbon-nanotube emitter.

15. The method of claim 11, wherein the array comprises multiple rows of electron-emitting sections, wherein each row is individually addressable.

16. The method of claim 11, wherein each electron-emitting section is individually addressable.

17. A method for radiographic imaging, the method comprising:

activating a first subset of electron-emitting sections of a cathode of a radiation source;

directing radiation emitted from the radiation source to a location on a target;

moving the radiation source relative to the target; and while moving the radiation source, deactivating the first subset of the electron-emitting sections and activating a second subset of electron-emitting sections to maintain the location on the target.

18. The method of claim 17, wherein the second subset of electron-emitting sections includes electron-emitting sections from the first subset of electron-emitting sections.

19. The method of claim 17, wherein the cathode comprises multiple rows of electron-emitting sections, and each row is individually addressable.

20. The method of claim 17, wherein each electron-emitting section comprises a single emitter that is individually addressable.

21. A radiation source, for use in radiographic imaging, comprising a cathode including a three-dimensional addressable array comprising a plurality of cathode plates having a plurality of addressable electron-emitting sections, wherein electron density emitted from the cathode is greater than an electron density that would be produced from the cathode plates if the cathode plates were arranged in a two-dimensional configuration.

22. The radiation source of claim 21, wherein the three-dimensional addressable array is a v-shaped three-dimensional array.

23. The radiation source of claim 21, wherein the three-dimensional addressable array is a pyramidal three-dimensional array.

24. The radiation source of claim 23, wherein the pyramidal three-dimensional array includes at least four cathode plates.

25. The radiation source of claim 24, where a first pair of the cathode plates are configured to linearly move a focal spot of the electrons emitted from the cathode and a second pair of cathode plates are configured to direct electrons emitted from the first pair of the cathode plates.

* * * * *